(12) United States Patent
Winter et al.

(10) Patent No.: US 9,550,160 B2
(45) Date of Patent: Jan. 24, 2017

(54) METHODS FOR PRODUCING NANOPARTICLES AND USING SAME

(71) Applicant: THE OHIO STATE UNIVERSITY RESEARCH FOUNDATION, Columbus, OH (US)

(72) Inventors: Jessica O Winter, Columbus, OH (US); Gang Ruan, Columbus, OH (US); Barbara Wyslouzil, Upper Arlington, OH (US); Anthony David Duong, Columbus, OH (US); Kalpesh Mahajan, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 594 days.

(21) Appl. No.: 13/629,552

(22) Filed: Sep. 27, 2012

(65) Prior Publication Data
US 2013/0078469 A1   Mar. 28, 2013

Related U.S. Application Data

(60) Provisional application No. 61/539,532, filed on Sep. 27, 2011, provisional application No. 61/541,462, filed on Sep. 30, 2011.

(51) Int. Cl.
*B01J 13/04* (2006.01)
*C09K 11/06* (2006.01)
(Continued)

(52) U.S. Cl.
CPC ............ *B01J 13/04* (2013.01); *A61K 9/5153* (2013.01); *C09K 11/06* (2013.01); *H01F 1/0045* (2013.01);
(Continued)

(58) Field of Classification Search
None
See application file for complete search history.

(56) References Cited

U.S. PATENT DOCUMENTS

| | | | |
|---|---|---|---|
| 6,007,845 | A | 12/1999 | Domb et al. |
| 6,252,129 | B1 | 6/2001 | Coffee |

(Continued)

FOREIGN PATENT DOCUMENTS

| | | |
|---|---|---|
| WO | 2008/121077 | 10/2008 |
| WO | 2008/137733 | 11/2008 |

OTHER PUBLICATIONS

International Search Report and Written Opinion for Application No. PCT/US12/57672 dated Jun. 5, 2013 (14 pages).
(Continued)

*Primary Examiner* — Jeffrey Washville
(74) *Attorney, Agent, or Firm* — Michael Best & Friedrich LLP

(57) ABSTRACT

A method for producing nanocomposite particles is provided. The method comprises supplying an organic phase fluid an organic phase fluid, an aqueous phase fluid, an amphiphile, and a plurality of hydrophobic nanospecies to a nozzle. An electric field is generated proximate the nozzle such that the fluid exiting the nozzle forms a cone jet that disperses into a plurality of droplets. The plurality of droplets are collected, and nanocomposite particles comprising a self-assembled structure encapsulating at least one hydrophobic nanospecies form by self-assembly.

3 Claims, 9 Drawing Sheets

(51) Int. Cl.
| | |
|---|---|
| H01F 1/00 | (2006.01) |
| B32B 5/16 | (2006.01) |
| B82Y 40/00 | (2011.01) |
| B82Y 30/00 | (2011.01) |
| A61K 9/51 | (2006.01) |
| B22F 1/00 | (2006.01) |

(52) U.S. Cl.
CPC ............ *B22F 1/0018* (2013.01); *B22F 1/0062* (2013.01); *B82Y 30/00* (2013.01); *B82Y 40/00* (2013.01); *H01F 1/0036* (2013.01); *Y10T 428/2989* (2015.01)

(56) References Cited

U.S. PATENT DOCUMENTS

| | | | |
|---|---|---|---|
| 2004/0033345 | A1 | 2/2004 | Dubertret et al. |
| 2005/0130167 | A1 | 6/2005 | Bao et al. |
| 2005/0136258 | A1* | 6/2005 | Nie .................. A61K 47/48861 428/402 |
| 2006/0083781 | A1* | 4/2006 | Shastri et al. ................. 424/450 |
| 2008/0242774 | A1 | 10/2008 | Lahann et al. |
| 2009/0203148 | A1 | 8/2009 | Gorfinkel et al. |
| 2011/0194304 | A1 | 8/2011 | Han et al. |
| 2012/0070376 | A1* | 3/2012 | Ostroff et al. ................. 424/9.1 |

OTHER PUBLICATIONS

Wu et al., "Immunofluorescent labeling of cancer marker Her2 and other cellular targets with semiconductor quantum dots," Nature Biotechnology, 2003. 21(1): p. 41-46.
Ballou et al., "Noninvasive imaging of quantum dots in mice. Bioconjugate Chemistry," 2004. 15(1): p. 79-86.
Dubertret et al., "In vivo imaging of quantum dots encapsulated in phospholipid micelles. Science," 2002. 298 (5599): p. 1759-1762.
Fan et al., "Surfactant-Assisted Synthesis of Water-Soluble and Biocompatible Semiconductor Quantum Dot Micelles," Nano Letters, 2005. 5(4): p. 645-648.
Chen et al., "Encapsulation of Single Small Gold Nanoparticles by Diblock Copolymers," ChemPhysChem, 2008. 9(3): p. 388-392.
Gao et al., "In vivo cancer targeting and imaging with semiconductor quantum dots," Nature Biotechnology, 2004. 22 (8): p. 969-976.
Han et al., "Quantum-dot-tagged microbeads for multiplexed optical coding of biomolecules," Nature Biotechnology, 2001. 19(7): p. 631-5.
Gao et al., "Quantum-dot nanocrystals for ultrasensitive biological labeling and multicolor optical encoding," J Biomed Opt, 2002. 7(4): p. 532-7.
Gao et al., "Doping Mesoporous Materials with Multicolor Quantum Dots," The Journal of Physical Chemistry B, 2003. 107(42): p. 11575-11578.
Salgueriño-Maceira et al., "Composite silica spheres with magnetic and luminescent functionalities," Advanced Functional Materials, 2006. 16(4): p. 509-514.
Yi et al., "Silica-Coated Nanocomposites of Magnetic Nanoparticles and Quantum Dots," Journal of the American Chemical Society, 2005. 127(14): p. 4990-4991.
Insin et al., "Incorporation of Iron Oxide Nanoparticles and Quantum Dots into Silica Microspheres," ACS Nano, 2008. 2(2): p. 197-202.
Kim et al., "Magnetomicelles: Composite Nanostructures from Magnetic Nanoparticles and Cross-Linked Amphiphilic Block Copolymers," Nano Letters, 2005. 5(10): p. 1987-1991.
Yusuf et al., "Size Control of Mesoscale Aqueous Assemblies of Quantum Dots and Block Copolymers," Langmuir, 2007. 23(2): p. 868-878.
Liu et al., "Preparation and characterization of novel fluorescent nanocomposite particles: CdSe/ZnS core-shell quantum dots loaded solid lipid nanoparticles," Journal of Biomedical Materials Research Part A, 2008, 84(4): p. 1018-25.
Chan et al., "Luminsecent quantum dots for multiplexed biological detection and imaging. Current Opinion in Biotechnology," 2002, 13(1): p. 40-46.
Park et al., "Micellar Hybrid Nanoparticles for Simultaneous Magnetofluorescent Imaging and Drug Delivery," Angew. Chem. Int. Ed., 2008, 47, 7284-7288.
European Patent Office Supplementary Partial Search Report for Application No. 12865220 dated Aug. 17, 2015 (7 pages).
European Patent Office Supplementary Partial Search Report for Application No. 12865220 dated Oct. 26, 2015 (13 pages).
Yu et al., "Solid lipid nannoparticles self-assembled from electrosprayed polymer-based microparticles," Journal of Materials Chemistry, 2011, vol. 21, No. 40, 15957.
Chinese Patent Office Action for Application No. 201280056969.X dated Mar. 4, 2016 (13 pages, English translation included).

* cited by examiner (a) (b) (c)

METHODS FOR PRODUCING NANOPARTICLES AND USING SAME

CROSS-REFERENCE TO RELATED APPLICATIONS

This application claims priority to, and the benefit of, U.S. Provisional Application No. 61/539,532, filed Sep. 27, 2011, and U.S. Provisional Application No. 61/541,462, filed on Sep. 30, 2011, the contents of which are incorporated herein by reference in their entirety.

STATEMENT REGARDING FEDERALLY SPONSORED RESEARCH

This invention is supported, at least in part, by Grant Nos. CBET-0707969, CMMI-090037, and EEC-0914790 awarded by the National Science Foundation. The government has certain rights in the invention.

FIELD OF THE DISCLOSURE

The general inventive concepts relate to nanoparticles, methods for producing nanoparticles, and methods of using the same. More particularly, the general inventive concepts relate to nanocomposite particles, polymeric nanoparticles, methods for producing nanocomposite particles and polymeric nanoparticles, and methods of using the same.

BACKGROUND OF THE DISCLOSURE

Nanotechnology is increasingly becoming a key field of technology owing to its diverse variety of potential applications. Such applications include medicine, biomedicine, electronics, biotechnology, biomaterials, biomechanics, and energy production, just to name a few. A number of methods utilized to produce nanomaterials focus on top-down approaches where large structures are used to assemble smaller structures. Bottom-up approaches also exist where atoms, ions, or molecules are selectively assembled to create useful structures. Current nanoparticle production methods are often limited to small scale batches, which hinder large scale applications.

SUMMARY OF THE DISCLOSURE

The general inventive concepts contemplate systems, apparatuses, and methods relating to the production of nanoparticles, as well as methods of using the nanoparticles. More specifically, the general inventive concepts contemplate nanocomposite particles, polymeric nanoparticles, methods for producing nanocomposite particles and polymeric nanoparticles, and methods of using the same.

In one exemplary embodiment, a method for producing nanocomposite particles is disclosed. The method comprises supplying an organic phase fluid to a nozzle. In certain embodiments, the organic phase fluid comprises an organic solvent, an amphiphile, and a plurality of hydrophobic nanospecies. An electric field is generated proximate the nozzle such that the fluid exiting the nozzle forms a cone jet that disperses into a plurality of droplets. The plurality of droplets is collected in an aqueous collection solution. In the aqueous collection solution, the nanocomposite particles self-assemble and comprise an amphiphilic micelle encapsulating at least one hydrophobic nanoparticle.

In one exemplary embodiment, a method for producing polymeric nanoparticles is disclosed. The method comprises supplying an organic phase fluid to a nozzle. In certain embodiments, the organic phase fluid comprises an organic solvent, an amphiphile, and a hydrophobic polymer. An electric field is generated proximate the nozzle such that the fluid exiting the nozzle forms a cone-jet that disperses into a plurality of droplets. The plurality of droplets is collected in an aqueous collection solution. In the aqueous collection solution, the polymeric nanoparticles self-assemble and comprise an amphiphilic micelle encapsulating the hydrophobic polymer.

In one exemplary embodiment, a nanocomposite particle is disclosed. The nanocomposite particle comprises a micelle comprising an amphiphile. At least one first quantum dot is encapsulated in the micelle, and the first quantum dot has a first emission wavelength. At least one second quantum dot is encapsulated in the micelle, and the second quantum dot has a second emission wavelength that is different from the first emission wavelength. The nanocomposite particle has a diameter within a range of 5 nm to 1000 nm. In one exemplary embodiment, the first emission wavelength is within a range of 490 nm to 560 nm and the second emission wavelength is within a range of 590 nm to 700 nm.

Other aspects, advantages, and features of the general inventive concepts will become apparent to those skilled in the art from the following detailed description, when read in light of the accompanying drawings.

BRIEF DESCRIPTION OF THE DRAWINGS

For a fuller understanding of the nature and advantages of the general inventive concepts, reference should be had to the following detailed description taken in connection with the accompanying drawings, in which.

DETAILED DESCRIPTION

Figure 1:
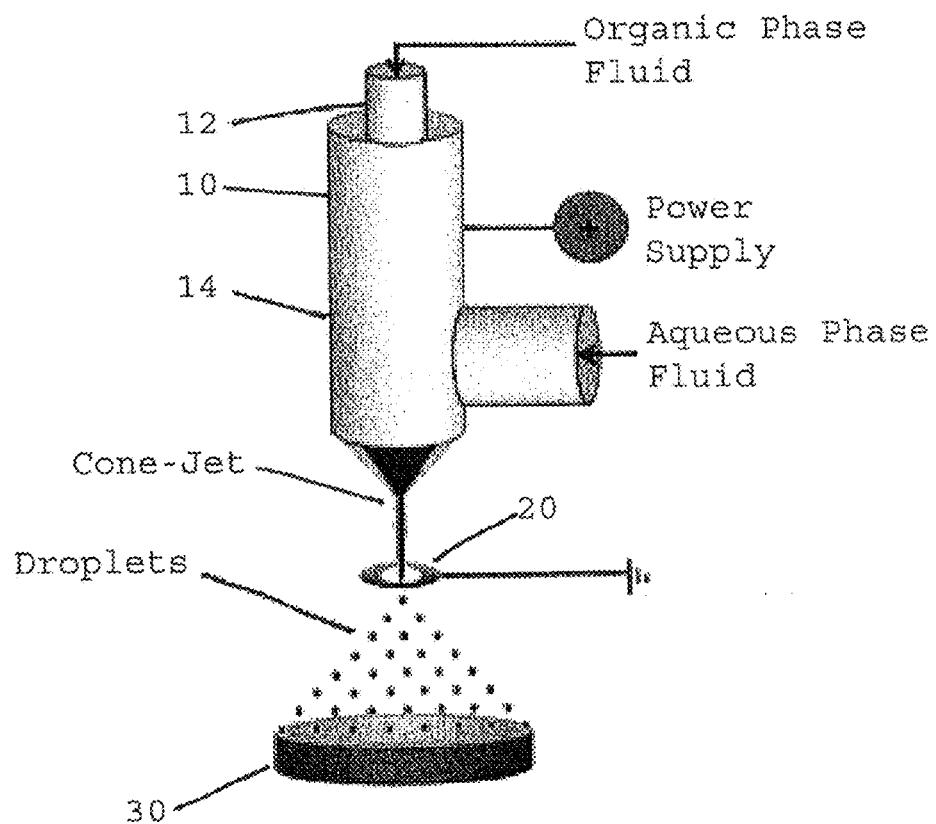
FIG. 1 schematically illustrates one exemplary embodiment of a method for producing nanocomposite particles or a method for producing polymeric nanoparticles.

While the general inventive concepts are susceptible of embodiment in many different forms, there are shown in the drawings, and will be described herein in detail, specific embodiments thereof with the understanding that the present disclosure is to be considered as an exemplification of the principles of the general inventive concepts. Accordingly, the general inventive concepts are not intended to be limited to the specific embodiments illustrated herein.

Unless otherwise defined, the terms used herein have the same meaning as commonly understood by one of ordinary skill in the art encompassing the general inventive concepts. The terminology used herein is for describing exemplary embodiments of the general inventive concepts only and is not intended to be limiting of the general inventive concepts. As used in the description of the general inventive concepts and the appended claims, the singular forms "a," "an," and "the" are intended to include the plural forms as well, unless the context clearly indicates otherwise.

Referring now to FIG. 1, a schematic illustration of a method for producing nanocomposite particles according to one exemplary embodiment is shown. In general, the method for producing nanocomposite particles employs an electrospray process for forming a plurality of droplets (e.g., a fine aerosol). As seen in FIG. 1, an organic phase fluid is supplied to a nozzle (10). In certain embodiments, the organic phase fluid comprises an organic solvent, an amphiphile, and a plurality of hydrophobic nanospecies. The nozzle (10) may have any number of configurations. For example, in one exemplary embodiment, the nozzle (10) is a coaxial nozzle having an inner tube (12) and an outer annulus (14). In other embodiments, the nozzle (10) may have multiple inner tubes (12) and an outer annulus (14).

As mentioned above, in certain embodiments the organic phase fluid comprises an organic solvent, an amphiphile, and a plurality of hydrophobic nanospecies. The organic phase fluid can be supplied via gravity feed or mechanical means, such as a pump, or syringe pump. In certain embodiments of the general inventive concepts, the organic phase fluid is supplied to the nozzle (10) at a flow rate of about 0.01 ml/hr to about 10 ml/hr. In one exemplary embodiment, the organic phase fluid is supplied to the nozzle (10) at a flow rate of about 0.48 ml/hr. A wide variety of organic solvents may be utilized. In general, the organic solvent may be polar or non-polar to dissolve any additional components of the organic phase fluid. Non-limiting examples of organic solvents that may be utilized in connection with the general inventive concepts described herein include, but are not limited to, chloroform, tetrahydrofuran, dichloromethane, and combinations thereof.

In addition, a wide variety of amphiphiles may be used in connection with the general inventive concepts described herein. The term "amphiphile," as used herein, refers to a chemical compound that includes a hydrophilic segment and a hydrophobic segment. In certain embodiments of the general inventive concepts, the amphiphile is an amphiphilic block copolymer. In certain other embodiments of the general inventive concepts, the amphiphile is a peptide amphiphile. Suitable amphiphilic block copolymers include, but are not limited to, poly(styrene-b-ethylene glycol), poly(ε-caprolactone-b-ethylene glycol), poly(ethylene glycol-b-distearoyl phophatidylethanolamine), and combinations thereof. Suitable peptide amphiphiles include, but are not limited to, palmitoyl-VVAAEE-NH2, palmitoyl-VVAAEEGIKVAV-COOH, palmitoyl-VVAAEEEEGIK-VAV-COOH, and combinations thereof. Those of skill in the art will appreciate that various other amphiphiles may be utilized and are within the scope of the general inventive concepts contemplated herein.

In certain embodiments, the organic phase fluid also includes a plurality of hydrophobic nanospecies. In certain exemplary embodiments according to the general inventive concepts described herein, the plurality of hydrophobic nanospecies can comprise one, two, three, four, or more different types of hydrophobic nanospecies. The nanospecies may be naturally hydrophobic or may be modified to have a hydrophobic surface or otherwise rendered hydrophobic. In certain exemplary embodiments of the general inventive concepts, the plurality of hydrophobic nanospecies includes, but is not limited to, semiconducting nanoparticles, metallic nanoparticles, magnetic nanoparticles, carbonaceous nanoparticles, and combinations thereof. Non-limiting examples of such hydrophobic nanoparticles include quantum dots, gold nanoparticles, silver nanoparticles, platinum nanoparticles, iron oxide nanoparticles, superparamagnetic iron oxide nanoparticles, carbon nanotubes, and carbon dots. The various combinations of the types of hydrophobic nanospecies utilized depend primarily on the desired function or application of the resulting nanocomposite particles (e.g., magnetic, fluorescent, magnetic and fluorescent, etc.).

Figure 2:
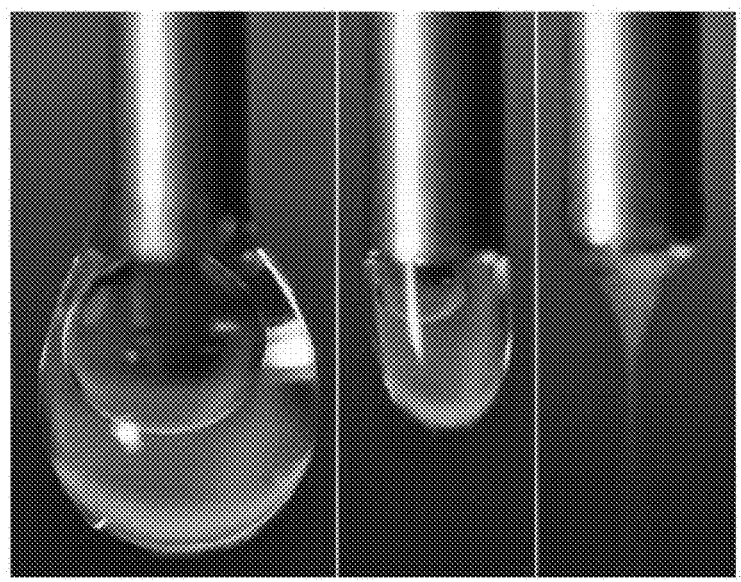
FIG. 2 illustrates the effect of an electric field on the meniscus of a fluid exiting a nozzle; (a) illustrates the meniscus of the fluid exiting the nozzle without the influence of an electric field; (b) illustrates the effect of a small electric field on the fluid exiting the nozzle, as seen by the deforming meniscus; (c) illustrates the effect of a larger electric field on the fluid exiting the nozzle, as seen by the deformation of the meniscus into a cone-jet.

Still referring to FIG. 1, when the organic phase fluid is supplied to the nozzle (10), an electric field is generated proximate the nozzle (10), particularly at a tip of the nozzle (10) where the fluid exits. In certain embodiments, an electric potential is applied to the nozzle (10) and an electric potential is applied to a grounded electrode (20) to generate the electric field proximate the nozzle (10). The electric field causes the fluid exiting the nozzle (10) to form a cone-jet that disperses into a plurality of droplets. In effect, the electric field exerts a force on the fluid exiting the nozzle (10) and deforms the meniscus of the fluid. For example, as seen in FIG. 2A, fluid is exiting the nozzle (10) without an electric field. In FIG. 2B, the meniscus of the fluid begins to deform after an electric field is generated proximate the nozzle. As seen in FIG. 2C, when the electric field is high enough, it will exert a force that is greater than a limit based on the surface tension of the fluid such that the meniscus adopts a cone shape with a thin jet of the fluid. The thin jet then breaks up into a plurality of droplets of the fluid.

In certain embodiments of the general inventive concepts described herein, the electric field is generated by a power supply used to create an electric potential between the coaxial nozzle (10) and the grounded electrode (20), which may be a ring formed of copper or other conductive metals. In one exemplary embodiment, the grounded electrode (20) is positioned 0.5 cm below the tip of the coaxial nozzle (10). In certain exemplary embodiments, the electric field that is generated has an electric field strength within a range of about 3 kV/cm to about 35 kV/cm. In one exemplary embodiment, the electric field that is generated has an electric field strength within a range of about 6 kV/cm to about 7 kV/cm.

In certain embodiments, as the plurality of droplets is formed from the dispersion of the cone-jet, the plurality of droplets are collected in an aqueous collection solution. In an exemplary embodiment, the aqueous collection solution comprises distilled water or double distilled water. In certain other embodiments according to the general inventive concepts described herein, the aqueous collection solution comprises ammonium acetate buffer. However, other types of aqueous solutions may be utilized and are contemplated by the general inventive concepts disclosed herein. In certain embodiments, the plurality of droplets are dispersed into a collector (30) containing the aqueous collection solution. The collector (30) may be a metal container, such as an aluminum dish, for example. In other embodiments, the plurality of droplets are dispersed directly into the aqueous collection solution without being exposed to the air, such as by submerging the nozzle in the aqueous collection solution.

After the plurality of droplets enters the aqueous collection solution, the nanocomposite particles self-assemble in the aqueous collection solution. The nanocomposite particles comprise an amphiphilic micelle encapsulating at least one hydrophobic nanoparticle. In one exemplary embodiment, the nanocomposite particles have an average diameter in a range of about 5 nm to about 1000 nm. In another exemplary embodiment, the nanocomposite particles have an average diameter in a range of about 10 nm to about 800 nm, including about 20 nm to about 700 nm, including about 25 nm to about 500 nm, including about 30 nm to about 100 nm, including about 30 nm to about 70 nm, and also including about 30 nm to about 50 nm. Such nanocomposite particles are useful for various applications including, but not limited to, imaging, therapeutic, and diagnostic applications, which will be discussed in further detail below.

As briefly mentioned above, in certain embodiments, the nanocomposite particles comprise amphiphilic micelles that can encapsulate multiple and diverse types of hydrophobic nanospecies. The amphiphilic micelles form by self-assembly of the amphiphile via interfacial instability when dispersed into the aqueous collection solution. As used herein, the term "amphiphilic micelle" refers to any self-assembled structure comprising an amphiphile. For example, when the plurality of droplets enter into the aqueous solution, the amphiphiles spontaneously orient to form micelles having a hydrophilic shell and a hydrophobic core. During the micelle formation, the hydrophobic nanospecies present are attracted to the hydrophobic segment of the amphiphile such that as the micelles are self-assembling the hydrophobic nanospecies are drawn to and encapsulated within the hydrophobic core of the micelle. It will be appreciated that the micelles will only encapsulate those hydrophobic nanospecies that are smaller than the hydrophobic core of the micelle.

The size and shape of the resulting nanocomposite particle may be controlled by the amphiphile utilized. For example, poly(styrene-b-ethylene glycol) with molecular weight of 3800-b-6500 Dalton and 9500-b-18000 Dalton leads to nanocomposite particles with diameters of 25 nm and 40 nm, respectively. Other amphiphiles, such as DSPE (distearoyl phosphatidylethanolamine)-co-polyethylene glycol (PEG) 2,000 form micelles having a diameter of 15 nm with a core diameter of 6.5 nm. Thus, when engineering nanocomposite particles for specific applications requiring a particular size of particles, the size of the nanocomposite particle can be controlled by selecting an appropriate amphiphile. Moreover, amphiphilic block copolymers are particularly advantageous because these materials generally have a relatively long hydrophobic segment. The longer hydrophobic segment allows for the formation of amphiphilic micelles having a larger hydrophobic core so that multiple and diverse types of hydrophobic nanospecies can be encapsulated within the micelle, while at the same time remaining small enough (<100 nm) to be particularly useful in various diverse applications.

As mentioned above, in certain embodiments according to the general inventive concepts, a coaxial nozzle (10) having an inner tube (12) and an outer annulus (14) is utilized. For example, in certain embodiments, coaxial nozzle (10) comprises an inner needle and an outer needle. The inner diameter of the inner needle may range from about 80 microns to about 800 microns, and the corresponding inner diameter of the outer needle may range from about 200 microns to about 2000 microns. In one exemplary embodiment, the method for producing nanocomposite particles further comprises supplying an aqueous phase fluid to the nozzle (10). In certain embodiments, the aqueous phase fluid comprises a surfactant. A wide variety of surfactants may be utilized in the aqueous phase fluid. Suitable examples of surfactants that may be utilized in connection with the general inventive concepts described herein include, but are not limited to, polyvinyl alcohol, octylphenol ethoxylate, 4-(5-Dodecyl) benzenesulfonate, sodium stearate, poloxamers, polysorbates, and combinations thereof. The aqueous phase fluid can be supplied via gravity feed or mechanical means, such as a pump, or syringe pump. In certain embodiments, the aqueous phase fluid is supplied to the nozzle (10) at a flow rate of 0.01 ml/hr to 10 ml/hr. In one exemplary embodiment, the aqueous phase fluid is supplied to the nozzle (10) at a flow rate of 2.8 ml/hr.

In one exemplary embodiment, the organic phase fluid is supplied to the inner tube (12) of the coaxial nozzle (10), and the aqueous phase fluid is supplied to the outer annulus (14) of the coaxial nozzle (10). In this exemplary configuration, the organic phase fluid is encapsulated by the aqueous phase fluid upon exiting the nozzle. The aqueous phase fluid therefore acts somewhat as a barrier that prevents significant evaporation of the organic phase fluid during the transit time of the fluid exiting the nozzle and entering the aqueous collection solution. In other embodiments, the organic phase fluid may be supplied to the outer annulus (14) of the coaxial nozzle (10) and the aqueous phase fluid may be supplied to the inner tube (12) of the coaxial nozzle (10).

In one exemplary embodiment, when the organic phase fluid supplied to the inner tube (12) of the coaxial nozzle (10), and the aqueous phase fluid supplied to the outer annulus (14) of the coaxial nozzle (10) achieve a stabilized flow exiting the coaxial nozzle (10), an electric field is generated proximate the nozzle (10), particularly at a tip of the nozzle (10) where the fluid exits. In certain embodiments, an electric potential is applied to the nozzle (10) and an electric potential is applied to a grounded electrode (20) to generate the electric field proximate the nozzle (10). As previously mentioned, the electric field causes the meniscus of the fluid exiting the nozzle (10) to adopt a cone shape with a thin jet of the fluid. The thin jet then breaks up into a plurality of droplets, which are collected in the aqueous collection solution and the nanocomposite particles are formed via self-assembly, as described above. In certain embodiments, the plurality of droplets comprises organic phase fluid encapsulated by aqueous phase fluid.

In certain embodiments contemplated by the general inventive concepts, the method of producing nanocomposite particles includes mixing or stirring the aqueous collection solution containing the plurality of droplets. The mixing or stirring step may better disperse the plurality of droplets within the aqueous collection solution to aid in the formation of the nanocomposite particles.

In one exemplary embodiment according to the general inventive concepts described herein, the nanocomposite particles comprise at least one first quantum dot having a first emission wavelength and at least one second quantum dot having a second emission wavelength that is different from the first emission wavelength. As used herein, the term "quantum dots" refers to semiconductor nanocrystals having unique optical properties such as broad excitation spectra, narrow emission bandwidths, and enhanced photostability. Quantum dots generally have a diameter of about 2 nm to about 10 nm. In one exemplary embodiment, the at least one first quantum dot has a first emission wavelength between 490 nm to 560 nm and the at least one second quantum dot has a second emission wavelength between 590 nm to 700 nm, and the nanocomposite particles have an average diameter in a range of 5 nm to 1000 nm. In certain embodiments, the nanocomposite particles comprising at least one first quantum dot having a first emission wavelength and at least one second quantum dot having a second emission wavelength have an average diameter in a range of about 10 nm to about 800 nm, including about 20 nm to about 700 nm, including about 25 nm to about 500 nm, including about 30 nm to about 100 nm, including about 30 nm to about 70 nm, and also including about 30 nm to about 50 nm.

Although the exemplary embodiment utilizes at least one first quantum dot having a first emission wavelength between about 490 nm to about 560 nm (i.e., green color) and at least one second quantum dot having a second emission wavelength between about 590 nm to about 700 nm (i.e., red color), various other combinations of quantum dots having different emission wavelengths (i.e., colors) may be utilized in connection with the general inventive concepts described herein. For example, the emission wavelengths may range from about 380 nm to about 800 nm, also including infrared. In certain embodiments, the first emission wavelength may be about 380 nm to about 450 nm, or about 450 nm to about 495 nm, or about 495 nm to about 570 nm, or about 570 nm to about 590 nm, or about 590 nm to about 620 nm, or about 620 nm to about 750 nm, and the second emission wavelength may be within any one of the aforementioned ranges that is not the same range as the first emission wavelength. By providing a second emission wavelength that is different from the first emission wavelength the colors emitted by the quantum dots encapsulated within the nanocomposite particles are able to be distinguished, which is particularly useful in particle tracking applications, as described in more detail below.

In accordance with the general inventive concepts, in one exemplary embodiment, a nanocomposite particle comprising a micelle comprising an amphiphile is provided. The nanocomposite particle also comprises at least one first quantum dot encapsulated in the micelle, and the first quantum dot has a first emission wavelength. In addition, the nanocomposite particle comprises at least one second quantum dot encapsulated in the micelle, and the second quantum dot has a second emission wavelength that is different from the first emission wavelength. The nanocomposite particle has a diameter in a range of about 5 nm to about 1000 nm. In certain embodiments, the nanocomposite particles have an average diameter in a range of about 10 nm to about 800 nm, including about 20 nm to about 700 nm, including about 25 nm to about 500 nm, including about 30 nm to about 100 nm, including about 30 nm to about 70 nm, and also including about 30 nm to about 50 nm. As mentioned above, the emission wavelengths may range from about 380 nm to about 800 nm, also including infrared, and the second emission wavelength is different from the first emission wavelength so that the colors emitted are able to be distinguished.

Nanocomposite particles comprising at least one first quantum dot having a first emission wavelength and at least one second quantum dot having a second emission wavelength that is different than the first emission wavelength are particularly useful for particle tracking applications, for example, particle tracking in heterogeneous systems such as living cells and microfluidic flow. By encapsulating quantum dots with differing emission wavelengths into a nanocomposite particle, two seemingly irreconcilable problems associated with quantum dots used for particle tracking are solved. The first problem associated with quantum dots is that quantum dots are subject to blinking, an intermittent loss of fluorescence (characteristic of individual and small clusters of quantum dots), that interrupts particle tracking. On the other hand, blinking is the primary method used to confirm quantum dot aggregation status in situ, and single or small clusters of quantum dots with continuous fluorescence emission are difficult to discern from large aggregates. In solving these two problems, the nanocomposite particles comprising at least one first quantum dot having a first emission wavelength and at least one second quantum dot having a second emission wavelength that is different than the first emission wavelength exhibit near-continuous, alternating-color fluorescence, which permits aggregation status discrimination by observable color changes even during motion across the focal plane.

Figure 3:
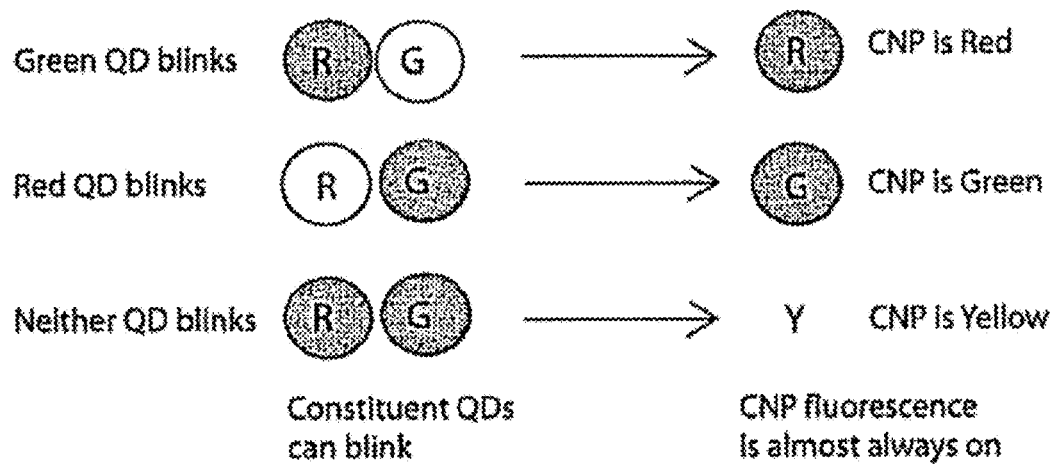
FIG. 3 shows a schematic of alternating fluorescence emission wavelength and near-continuous fluorescence in an exemplary nanocomposite particle (CNP)

Referring now to FIG. 3, because blinking dynamics are stochastic, a single exemplary nanocomposite particle comprising at least one first quantum dot having a first emission wavelength (e.g., 490 nm to 560 nm—green color) and at least one second quantum dot having a second emission wavelength that is different from the first emission wavelength (e.g., 590 nm to 700 nm—red color) remains nearly continuously fluorescent while the emission wavelength alternates between those of the first and second quantum dots, and their combinations. In contrast, large aggregates of the nanocomposite particles will display a nearly constant fluorescence emission color, which permits single nanocomposite particles (or very small clusters) to be distinguished by their alternating-color emission. Such nanocomposite particles, therefore, can be continuously tracked and identified as a single nanocomposite particle or a very small cluster of nanocomposite particles.

In addition, nanocomposite particles comprising at least one first quantum dot having a first emission wavelength and at least one second quantum dot having a second emission wavelength that is different than the first emission wavelength may be used to distinguish the nanocomposite particle from background fluorescence emitted in a wavelength channel that overlaps with the first emission wavelength or the second emission wavelength. For example, if there is too much background fluorescence at 500 nm, then it would still be possible to distinguish a nanocomposite particle comprising quantum dots having an emission wavelength of 490 nm to 560 nm and quantum dots having an emission wavelength of 590 nm to 700 nm by imaging at, for example, 650 nm.

In accordance with the general inventive concepts described herein, in one exemplary embodiment, the nanocomposite particle comprises an amphiphilic micelle encapsulating a plurality of quantum dots having the same emission wavelength. In this particular embodiment, the brightness of the fluorescence emission is increased without increasing the size of nanocomposite particle.

In one exemplary embodiment of the general inventive concepts, the nanocomposite particle comprising an amphiphilic micelle encapsulating at least one first quantum dot having a first emission wavelength and at least one second quantum dot having a second emission wavelength that is different from the first emission wavelength further comprises at least one additional nanospecies encapsulated in the micelle. For example, the at least one additional nanospecies includes, but is not limited to, nanospecies selected from the group consisting of magnetic nanoparticles, metallic nanoparticles, carbonaceous nanoparticles, and combinations thereof. The additional nanospecies increases the functionality of the nanocomposite particle (e.g., a magnetic nanoparticle enables manipulation of the nanocomposite particle by a magnetic field) to broaden the applications of the nanocomposite particles.

According to the general inventive concepts described herein, in one exemplary embodiment, the nanocomposite particle comprises at least one quantum dot and at least one magnetic nanoparticle, and the nanocomposite particles have an average diameter in a range of about 5 nm to about 1000 nm. The magnetic nanoparticle may comprise an iron oxide nanoparticle, a superparamagnetic iron oxide nanoparticles, or various other magnetic nanoparticles of iron, nickel, cobalt, compounds thereof, and combinations thereof. As mentioned above, in certain embodiments, the nanocomposite particles have an average diameter in a range of about 10 nm to about 800 nm, including about 20 nm to about 700 nm, including about 25 nm to about 500 nm, including about 30 nm to about 100 nm, including about 30 nm to about 70 nm, and also including about 30 nm to about 50 nm.

Nanocomposite particles comprising at least one quantum dot and at least one magnetic nanoparticle have a vast number of applications based upon their fluorescent and magnetic properties. The fluorescence imparted by the quantum dots allows the nanocomposite particles to used as imaging agents in traditional diagnostic applications (e.g., immunocytochemistry), whereas the magnetic property from the magnetic nanoparticles allows the nanocomposite particles to be manipulated by a magnetic field, which can lead to the design of magnetically targeted nanostructures. In addition, such nanocomposite particles can be used to isolate and characterize the molecular profiles of cancer cells, such as circulating tumor cells, and to perform mulitmodal in vivo tumor visualization through magnetic resonance and fluorescent imaging. Moreover, such nanocomposite particles can be used in vitro to manipulate and track cells, biomolecules, and nanostructures.

In one exemplary embodiment according to the general inventive concepts, the nanocomposite particles further comprise a functional group. More specifically, the functional group is conjugated to, bound to, or otherwise attached to the nanocomposite particle, or the nanocomposite particle is conjugated to, bound to, or otherwise attached to the functional group. The functional group can be virtually any molecule that is useful for biological, environmental, or various other applications. In certain embodiments of the general inventive concepts, the functional group is selected from the group consisting of a peptide, a polypeptide, a protein, a ligand, an antibody, DNA, RNA, and combinations thereof. However, the functional group may comprise virtually any compound or molecule designed to target and bind to, for example, specific types of cells, proteins, and so forth. Thus, the term "functional group," as used herein, broadly encompasses compounds or molecules designed to target a specific entity. In essence, a nanocomposite particle may be labeled with a functional group, or a functional group may be labeled with a nanocomposite particle. For example, in one exemplary embodiment, the nanocomposite particle is conjugated with an antibody that targets a specific cell population. There are several methods of crosslinking or conjugating or otherwise attaching proteins, ligands, antibodies, molecular fragments, and the like through chemical modifications known in the art that may be utilized in connection with the general inventive concepts described herein. For example, carbodiimide (EDC) chemistry or NHS-ester crosslinker chemistry may be utilized to conjugate, crosslink, bind, or otherwise attach a functional group to a nanocomposite particle, and vice versa.

In one exemplary embodiment according to the general inventive concepts, the method for producing nanocomposite particles comprises utilizing a plurality of nozzles. For example, the plurality of nozzles may be provided as a planar array of nozzles, which are operated in parallel, or in other suitable arrangements. In certain embodiments, the plurality of nozzles comprise coaxial nozzles, as previously described. Such an exemplary embodiment provides the method with scalability to increase the production of the nanocomposite particles.

In one exemplary embodiment according to the general inventive concepts disclosed herein, a method for producing nanocomposite particles comprises supplying an organic phase fluid, an aqueous phase fluid, an amphiphile, and a plurality of hydrophobic nanospecies to a nozzle. An electric field is generated proximate the nozzle such that the fluid exiting the nozzle forms a cone-jet that disperses into a plurality of droplets. The plurality of droplets are collected, and nanocomposite particles comprising a self-assembled structure encapsulating at least one hydrophobic nanospecies form by self-assembly.

In general, the organic phase fluid comprises an organic solvent. A wide variety of organic solvents may be utilized. In general, the organic solvent may be polar or non-polar to dissolve any additional components of the organic phase fluid. Non-limiting examples of organic solvents that may be utilized in connection with the general inventive concepts described herein include, but are not limited to, chloroform, tetrahydrofuran, dichloromethane, and combinations thereof. The organic phase fluid can be supplied via gravity feed or mechanical means, such as a pump, or syringe pump. In certain embodiments of the general inventive concepts, the organic phase fluid is supplied to the nozzle (10) at a flow rate of about 0.01 ml/hr to about 10 ml/hr. In one exemplary embodiment, the organic phase fluid is supplied to the nozzle (10) at a flow rate of about 0.48 ml/hr. In certain embodiments, the organic phase fluid further comprises a surfactant. A wide variety of surfactants may be utilized in the organic phase fluid. Suitable examples of surfactants that may be utilized in connection with the general inventive concepts described herein include, but are not limited to, polyvinyl alcohol, octylphenol ethoxylate, 4-(5-Dodecyl) benzenesulfonate, sodium stearate, poloxamers, polysorbates, and combinations thereof.

In general, the aqueous phase fluid comprises water. A wide variety of aqueous systems may be utilized as the aqueous phase fluid. In certain embodiments, the aqueous phase fluid further comprises a surfactant. A wide variety of surfactants may be utilized in the aqueous phase fluid. Suitable examples of surfactants that may be utilized in connection with the general inventive concepts described herein include, but are not limited to, polyvinyl alcohol, octylphenol ethoxylate, 4-(5-Dodecyl) benzenesulfonate, sodium stearate, poloxamers, polysorbates, and combinations thereof. The aqueous phase fluid can be supplied via gravity feed or mechanical means, such as a pump, or syringe pump. In certain embodiments, the aqueous phase fluid is supplied to the nozzle (10) at a flow rate of 0.01 ml/hr to 10 ml/hr. In one exemplary embodiment, the aqueous phase fluid is supplied to the nozzle (10) at a flow rate of 2.8 ml/hr.

As previously mentioned, a wide variety of amphiphiles may be used in connection with the general inventive concepts described herein. In certain embodiments of the general inventive concepts, the amphiphile is an amphiphilic block copolymer. In certain other embodiments of the general inventive concepts, the amphiphile is a peptide amphiphile. Suitable amphiphilic block copolymers include, but are not limited to, poly(styrene-b-ethylene glycol), poly(ε-caprolactone-b-ethylene glycol), poly(ethylene glycol-b-distearoyl phosphatidylethanolamine), and combinations thereof. Suitable peptide amphiphiles include, but are not limited to, palmitoyl-VVAAEE-NH2, palmitoyl-VVAAEEGIKVAV-COOH, palmitoyl-VVAAEEEEGIK-VAV-COOH, and combinations thereof. Those of skill in the art will appreciate that various other amphiphiles may be utilized and are within the scope of the general inventive concepts contemplated herein.

In certain embodiments according to the general inventive concepts described herein, the amphiphile is supplied to the nozzle in the organic phase fluid. For example, in certain embodiments, the amphiphile is dispersed, dissolved, or otherwise added to the organic phase fluid. In certain other embodiments, the amphiphile is supplied directly to the nozzle. For example, the amphiphile can be supplied directly to the nozzle via gravity feed or mechanical means, such as a pump, or syringe pump. In certain other embodiments, the amphiphile is supplied to the nozzle in the aqueous phase fluid. For example, in certain embodiments, the amphiphile is dispersed, dissolved, or otherwise added to the aqueous phase fluid.

As previously discussed, a wide variety of hydrophobic nanospecies may be utilized according to the general inventive concepts described herein. In certain embodiments, the plurality of hydrophobic nanospecies can comprise one, two, three, four, or more different types of hydrophobic nanospecies. The nanospecies may be naturally hydrophobic or may be modified to have a hydrophobic surface or otherwise rendered hydrophobic. In certain exemplary embodiments of the general inventive concepts, the plurality of hydrophobic nanospecies includes, but is not limited to, semiconducting nanoparticles, metallic nanoparticles, magnetic nanoparticles, carbonaceous nanoparticles, and combinations thereof. Non-limiting examples of such hydrophobic nanoparticles include quantum dots, gold nanoparticles, silver nanoparticles, platinum nanoparticles, iron oxide nanoparticles, superparamagnetic iron oxide nanoparticles, carbon nanotubes, and carbon dots. The various combinations of the types of hydrophobic nanospecies utilized depend primarily on the desired function or application of the resulting nanocomposite particles (e.g., magnetic, fluorescent, magnetic and fluorescent, etc.).

In certain embodiments, the plurality of hydrophobic nanospecies is supplied to the nozzle in the organic phase fluid. For example, the plurality of hydrophobic nanospecies is dispersed, dissolved, or otherwise added to the organic phase fluid. In certain embodiments, the plurality of hydrophobic nanospecies is supplied to the nozzle via the amphiphile. For example, the plurality of hydrophobic nanospecies is dispersed, dissolved, or otherwise added to the amphiphile. In certain other embodiments, the plurality of hydrophobic nanospecies is supplied to the nozzle in the aqueous phase fluid. For instance, the plurality of hydrophobic nanospecies is dispersed, dissolved, or otherwise added to the aqueous phase fluid.

As mentioned, an electric field is generated proximate the nozzle (10), particularly at a tip of the nozzle (10) where the fluid comprising the organic phase fluid, the aqueous phase fluid, the amphiphile, and the plurality of hydrophic nanospecies exits. In certain embodiments, an electric potential is applied to the nozzle (10) and an electric potential is applied to a grounded electrode (20) to generate the electric field proximate the nozzle (10). The electric field causes the fluid exiting the nozzle (10) to form a cone-jet that disperses into a plurality of droplets. In effect, the electric field exerts a force on the fluid exiting the nozzle (10) and deforms the meniscus of the fluid. As previously described, when the electric field is high enough, it will exert a force that is greater than a limit based on the surface tension of the fluid such that the meniscus adopts a cone shape with a thin jet of the fluid. The thin jet then breaks up into a plurality of droplets of the fluid.

In certain embodiments of the general inventive concepts described herein, the electric field is generated by a power supply used to create an electric potential between the coaxial nozzle (10) and the grounded electrode (20), which may be a ring formed of copper or other conductive metals. In one exemplary embodiment, the grounded electrode (20) is positioned 0.5 cm below the tip of the coaxial nozzle (10). In certain exemplary embodiments, the electric field that is generated has an electric field strength within a range of about 3 kV/cm to about 35 kV/cm. In one exemplary embodiment, the electric field that is generated has an electric field strength within a range of about 6 kV/cm to about 7 kV/cm.

As the plurality of droplets is formed from the dispersion of the cone-jet, the plurality of droplets are collected. In certain embodiments, the plurality of droplets are collected in an aqueous collection solution. In an exemplary embodiment, the aqueous collection solution comprises distilled water or double distilled water. In certain other embodiments according to the general inventive concepts described herein, the aqueous collection solution comprises ammonium acetate buffer. However, other types of aqueous solutions may be utilized and are contemplated by the general inventive concepts disclosed herein. In certain embodiments, the plurality of droplets are dispersed into a collector (30) containing the aqueous collection solution. The collector (30) may be a metal container, such as an aluminum dish, for example. In other embodiments, the plurality of droplets are dispersed directly into an aqueous collection solution without being exposed to the air, such as by submerging the nozzle in the aqueous collection solution.

In one exemplary embodiment, the plurality of droplets is collected on a surface. In other words, the plurality of droplets are dispersed directly onto a surface. Virtually any surface may be utilized to collect the plurality of droplets. For example, the plurality of droplets can be collected on a metal plate (e.g., aluminum plate), a transmission electron microscopy grid, or virtually any other type of surface.

In certain embodiments, after the plurality of droplets enters the aqueous collection solution, nanocomposite particles self-assemble in the aqueous collection solution. In one exemplary embodiment, the nanocomposite particles comprise a self-assembled structure encapsulating at least one hydrophobic nanospecies. For example, the self-assembled structure can comprise a micelle, or virtually any other self-assembling structure. The self-assembly is driven by interfacial instability. For example, in one embodiment, the amphiphiles orient to form a self-assembled structure having a hydrophilic shell and a hydrophobic core. During the formation of the self-assembled structure, the hydrophobic nanospecies present are attracted to the hydrophobic segments of the amphiphiles such that as the self-assembled structures are forming the hydrophobic nanospecies are drawn to and encapsulated within the hydrophobic core of the self-assembled structure. It will be appreciated that the self-assembled structures will only encapsulate those hydrophobic nanospecies that are smaller than the hydrophobic core of the self-assembled structure.

In certain embodiments, when the plurality of droplets is collected on a surface, nanocomposite particles self-assemble on the surface. In one exemplary embodiment, the nanocomposite particles comprise a self-assembled structure encapsulating at least one hydrophobic nanospecies. As mentioned above, the self-assembled structure can comprise a micelle, or other types of self-assembling structures. In this particular embodiment, the driving force for the self-assembly of the nanocomposite particles is provided by an organic phase-aqueous phase interface present in the plurality of droplets. In addition, self-assembly may be driven as the organic solvent is removed, such as by evaporation or diffusion.

In one exemplary embodiment according to the general inventive concepts contemplated herein, a method for producing polymeric nanoparticles is provided. In an exemplary embodiment, the method for producing polymeric nanoparticles employs an electrospray process for forming a plurality of droplets (e.g., a fine aerosol). The method for producing polymeric nanoparticles is similar to the previously discussed method for producing nanocomposite particles. As seen in FIG. 1, an organic phase fluid is supplied to a nozzle (10). In general, the organic phase fluid comprises an organic solvent. In an exemplary embodiment, the organic phase fluid comprises an organic solvent, an amphiphile, and a hydrophobic polymer. The nozzle (10) may have any number of configurations. For example, in one exemplary embodiment, the nozzle (10) is a coaxial nozzle having an inner tube (12) and an outer annulus (14). In other embodiments, the nozzle (10) may have multiple inner tubes (12) and an outer annulus (14).

As mentioned, in an exemplary embodiment, the organic phase fluid comprises an organic solvent, an amphiphile, and a hydrophobic polymer. The organic phase fluid can be supplied via gravity feed or mechanical means, such as a pump, or syringe pump. In certain embodiments of the general inventive concepts, the organic phase fluid is supplied to the nozzle (10) at a flow rate of 0.01 ml/hr to 10 ml/hr. In one exemplary embodiment, the organic phase fluid is supplied to the nozzle (10) at a flow rate of 0.48 ml/hr. A wide variety of organic solvents may be utilized. In general, the organic solvent may be polar or non-polar to dissolve any additional components of the organic phase fluid. Non-limiting examples of organic solvents that may be utilized in connection with the general inventive concepts described herein include, but are not limited to, chloroform, tetrahydrofuran, dichloromethane, and combinations thereof.

In certain embodiments of the method for producing polymeric nanoparticles, the amphiphile is an amphiphilic block copolymer. In certain other embodiments of the general inventive concepts, the amphiphile is a peptide amphiphile. Suitable amphiphilic block copolymers include, but are not limited to, poly(styrene-b-ethylene glycol), poly(ε-caprolactone-b-ethylene glycol), poly(ethylene glycol-b-distearoyl phophatidylethanolamine), and combinations thereof. Suitable peptide amphiphiles include, but are not limited to, palmitoyl-VVAAEE-NH2, palmitoyl-VVAAEEGIKVAV-COOH, palmitoyl-VVAAEEEGIK-VAV-COOH, and combinations thereof. Those of skill in the art will appreciate that various other amphiphiles may be utilized and are within the scope of the general inventive concepts contemplated herein.

In one exemplary embodiment, the organic phase fluid comprises a hydrophobic polymer. In certain embodiments, the hydrophobic polymer is biocompatible and biodegradable. For example, in one exemplary embodiment, the hydrophobic polymer is poly(lactic-co-glycolic acid). However, other hydrophobic polymers are contemplated in accordance with the general inventive concepts including, but not limited to, poly(lactic-co-glycolic acid), poly(lactic acid), poly(glycolic acid), poly(caprolactone), poly(ethylene glycol), and combinations thereof.

Still referring to FIG. 1, in certain embodiments, when the organic phase fluid is supplied to the nozzle (10), an electric field is generated proximate to the nozzle (10), particularly at a tip of the nozzle (10) where the fluid exits. In certain embodiments, an electric potential is applied to the nozzle (10) and an electric potential is applied to a grounded electrode (20) to generate the electric field proximate the nozzle (10). The electric field causes the fluid exiting the nozzle (10) to form a cone-jet that disperses into a plurality of droplets. In effect, the electric field exerts a force on the fluid exiting the nozzle (10) and deforms the meniscus of the fluid. As previously described with respect to FIG. 2C, when the electric field is high enough, it will exert a force that is greater than a limit based on the surface tension of the fluid such that the meniscus adopts a cone shape with a thin jet of the fluid. The thin jet then breaks up into a plurality of droplets of the fluid.

In certain embodiments of the general inventive concepts described herein, the electric field is generated by a power supply. The power supply creates an electric potential between the coaxial nozzle (10) and the grounded electrode (20), which may be a ring formed of copper or other conductive metals. In one exemplary embodiment, the grounded electrode (20) is positioned 0.5 cm below the tip of the coaxial nozzle (10). In certain exemplary embodiments, the electric field that is generated has an electric field strength within a range of about 3 kV/cm to about 35 kV/cm. In one exemplary embodiment, the electric field that is generated has an electric field strength within a range of about 6 kV/cm to about 7 kV/cm.

As the plurality of droplets is formed from the dispersion of the cone-jet, the plurality of droplets are collected in an aqueous collection solution. In an exemplary embodiment, the aqueous collection solution comprises distilled water or double distilled water. In certain other embodiments according to the general inventive concepts described herein, the aqueous collection solution comprises ammonium acetate buffer. However, other types of aqueous solutions may be utilized and are contemplated by the general inventive concepts disclosed herein. In certain embodiments, the plurality of droplets is dispersed into a collector (30) containing the aqueous collection solution. The collector (30) may be a metal container, such as an aluminum dish, for example. In other embodiments, the plurality of droplets are dispersed directly into the aqueous collection solution without being exposed to the air, such as by submerging the nozzle in the aqueous collection solution.

After the plurality of droplets enter the aqueous collection solution, the polymeric nanoparticles self-assemble in the aqueous collection solution. The polymeric naoparticles comprise an amphiphilic micelle encapsulating the hydrophobic polymer. In one exemplary embodiment, the polymeric nanoparticles have a diameter in a range of about 5 nm to about 1000 nm. In another exemplary embodiment, the nanocomposite particles have a diameter in a range of about 10 nm to about 800 nm, including about 20 nm to about 700 nm, including about 25 nm to about 500 nm, including about 30 nm to about 100 nm, and also including about 35 nm to about 70 nm. Such polymeric nanoparticles are particularly useful for controlled release delivery systems, which can increase therapeutic effects and decrease side effects.

As mentioned above, the polymeric nanoparticles comprise amphiphilic micelles that encapsulate the hydrophobic polymer. The amphiphilic micelles form by self-assembly of the amphiphile via interfacial instability when dispersed into the aqueous collection solution. For example, when the plurality of droplets enters the aqueous solution, the amphiphiles spontaneously orient to form micelles having a hydrophilic shell and a hydrophobic core. During the micelle formation, the particles of hydrophobic polymer present are attracted to the hydrophobic segment of the amphiphile such that as the micelles are self-assembling, the particles of the hydrophobic polymer are drawn to and encapsulated within the hydrophobic core of the micelle. In essence, the amphiphilic micelles form a particular sized "template," which can be used to control the size of the polymeric nanoparticles produced. As discussed in detail above, the size of the amphiphilic micelle, and thus the size of the polymeric nanoparticles, may be controlled by the particular amphiphile utilized. Moreover, because the self-assembly process is spontaneous, and because the self-assembled structures are thermodynamically stable, ultrasmall polymeric nanoparticles (<100 nm) can be created in a robust and reproducible process.

As mentioned above, in certain embodiments according to the general inventive concepts, a coaxial nozzle (10) having an inner tube (12) and an outer annulus (14) may be utilized in the method for producing polymeric nanoparticles. For example, in certain embodiments, coaxial nozzle (10) comprises an inner needle and an outer needle. The inner diameter of the inner needle may range from about 80 microns to about 800 microns, and the corresponding inner diameter of the outer needle may range from about 200 microns to about 2000 microns. In one exemplary embodiment, the method for producing polymeric nanoparticles further comprises supplying an aqueous phase fluid to the nozzle (10). In certain embodiments, the aqueous phase fluid comprises a surfactant. A wide variety of surfactants may be utilized in the aqueous phase fluid. Suitable examples of surfactants that may be utilized in connection with the general inventive concepts described herein include, but are not limited to, polyvinyl alcohol, octylphenol ethoxylate, 4-(5-Dodecyl) benzenesulfonate, sodium stearate, poloxamers, polysorbates, and combinations thereof. The aqueous phase fluid can be supplied via gravity feed or mechanical means, such as a pump, or syringe pump. In certain embodiments, the aqueous phase fluid is supplied to the nozzle (10) at a flow rate of 0.01 ml/hr to 10 ml/hr. In one exemplary embodiment, the aqueous phase fluid is supplied to the nozzle (10) at a flow rate of 2.8 ml/hr.

In one exemplary embodiment, the organic phase fluid is supplied to the inner tube (12) of the coaxial nozzle (10), and the aqueous phase fluid is supplied to the outer annulus (14) of the coaxial nozzle (10). In this exemplary configuration, the organic phase fluid is encapsulated by the aqueous phase fluid upon exiting the nozzle. The aqueous phase fluid therefore acts somewhat as a barrier that prevents significant evaporation of the organic phase fluid during the transit time of the fluid exiting the nozzle and entering the aqueous collection solution. In other embodiments, the organic phase fluid may be supplied to the outer annulus (14) of the coaxial nozzle (10) and the aqueous phase fluid may be supplied to the inner tube (12) of the coaxial nozzle (10).

In one exemplary embodiment, when the organic phase fluid supplied to the inner tube (12) of the coaxial nozzle (10), and the aqueous phase fluid supplied to the outer annulus (14) of the coaxial nozzle (10) achieve a stabilized flow exiting the coaxial nozzle (10), an electric field is generated proximate the coaxial nozzle (10), particularly near the tip of the nozzle where the fluid exits. The electric field generated proximate the nozzle causes the fluid exiting the coaxial nozzle (10) to form a cone-jet that disperses into a plurality of droplets. In certain embodiments, the plurality of droplets comprises the organic phase fluid encapsulated by aqueous phase fluid. As previously mentioned, the electric field causes the meniscus of the fluid exiting the nozzle (10) to adopt a cone shape with a thin jet of the fluid. The thin jet then breaks up into a plurality of droplets, which are collected in the aqueous collection solution and the polymeric nanoparticles are formed via self-assembly, as described above.

In certain embodiments contemplated by the general inventive concepts, the method of producing polymeric nanoparticles includes mixing or stirring the aqueous collection solution containing the plurality of droplets. The mixing or stirring step may better disperse the plurality of droplets within the aqueous collection solution to aid in the formation of the polymeric nanoparticles.

As previously noted, the polymeric nanoparticles of the contemplated general inventive concepts are useful for controlled release delivery systems. Accordingly, in one exemplary embodiment, the organic phase fluid further comprises an active ingredient, and the polymeric nanoparticles comprise self-assembled structures, such as amphiphilic micelles, encapsulating the hydrophobic polymer and the active ingredient. In another embodiment, the active ingredient may be supplied in the aqueous phase fluid. The active ingredient may be virtually any molecule or compound, including but not limited to, anticancer drugs, therapeutic proteins, antibiotics, skin care agents, fertilizers, and so forth. In an exemplary embodiment, the particle size of the polymeric nanoparticles (e.g., <100 nm) contemplated by the general inventive concepts described herein provides a number of advantages in the delivery of an active ingredient including, but not limited to, a better half-life in the blood stream, increased colloidal stability, faster release, deeper penetration into tissue, and so forth.

In one exemplary embodiment, the polymeric nanoparticles further comprise a functional group. The functional group can be virtually any molecule that is useful for biological, environmental, or various other applications. In certain embodiments of the general inventive concepts, the functional group is selected from the group consisting of a peptide, a polypeptide, a protein, a ligand, an antibody, DNA, RNA, and combinations thereof. However, the functional group may comprise virtually any compound or molecule designed to target and bind to, for example, specific types of cells, proteins, and so forth. Thus, the term "functional group," as used herein, broadly encompasses compounds or molecules designed to target a specific entity. The functional group may be conjugated to, bound to, crosslinked to, or otherwise attached to the polymeric nanoparticle. Similarly, the polymeric nanoparticle may be conjugated to, bound to, crosslinked to, or otherwise attached to the functional group. In essence, a polymeric nanoparticle may be labeled with a functional group, or a functional group may be labeled with a polymeric nanoparticle. For example, in one exemplary embodiment, the polymeric nanoparticle is conjugated with an antibody that targets a specific cell population. There are several methods of crosslinking or conjugating or otherwise attaching proteins, ligands, antibodies, molecular fragments, and the like through chemical modifications known in the art that may be utilized in connection with the general inventive concepts described herein. For example, carbodiimide (EDC) chemistry or NHS-ester crosslinker chemistry may be utilized to conjugate, crosslink, bind, or otherwise attach a functional group to a polymeric nanoparticle, and vice versa.

In an exemplary embodiment according to the general inventive concepts, the method for producing polymeric nanoparticles comprises utilizing a plurality of nozzles (10). For example, the plurality of nozzles (10) may be provided as a planar array of nozzles, which are operated in parallel. In certain embodiments, the plurality of nozzles may be coaxial nozzles, as previously described. Such an exemplary embodiment provides the method with scalability to increase the production of the polymeric nanoparticles.

In one exemplary embodiment according to the general inventive concepts disclosed herein, a method for producing polymeric nanoparticles comprises supplying an organic phase fluid, an aqueous phase fluid, an amphiphile, and a polymer to a nozzle. An electric field is generated proximate the nozzle such that the fluid exiting the nozzle forms a cone jet that disperses into a plurality of droplets. The plurality of droplets are collected, and polymeric nanoparticles comprising a self-assembled structure encapsulating the polymer form by self-assembly.

In general, the organic phase fluid comprises an organic solvent. A wide variety of organic solvents may be utilized. In general, the organic solvent may be polar or non-polar to dissolve any additional components of the organic phase fluid. Non-limiting examples of organic solvents that may be utilized in connection with the general inventive concepts described herein include, but are not limited to, chloroform, tetrahydrofuran, dichloromethane, and combinations thereof. The organic phase fluid can be supplied via gravity feed or mechanical means, such as a pump, or syringe pump. In certain embodiments of the general inventive concepts, the organic phase fluid is supplied to the nozzle (10) at a flow rate of about 0.01 ml/hr to about 10 ml/hr. In one exemplary embodiment, the organic phase fluid is supplied to the nozzle (10) at a flow rate of about 0.48 ml/hr. In certain embodiments of the method for producing polymeric nanoparticles, the organic phase fluid further comprises a surfactant. A wide variety of surfactants may be utilized in the organic phase fluid. Suitable examples of surfactants that may be utilized in connection with the general inventive concepts described herein include, but are not limited to, polyvinyl alcohol, octylphenol ethoxylate, 4-(5-Dodecyl) benzenesulfonate, sodium stearate, poloxamers, polysorbates, and combinations thereof.

In general, the aqueous phase fluid comprises water. A wide variety of aqueous systems may be utilized as the aqueous phase fluid. In certain embodiments of the method for producing polymeric nanoparticles, the aqueous phase fluid further comprises a surfactant. A wide variety of surfactants may be utilized in the aqueous phase fluid. Suitable examples of surfactants that may be utilized in connection with the general inventive concepts described herein include, but are not limited to, polyvinyl alcohol, octylphenol ethoxylate, 4-(5-Dodecyl) benzenesulfonate, sodium stearate, poloxamers, polysorbates, and combinations thereof. The aqueous phase fluid can be supplied via gravity feed or mechanical means, such as a pump, or syringe pump. In certain embodiments, the aqueous phase fluid is supplied to the nozzle (10) at a flow rate of 0.01 ml/hr to 10 ml/hr. In one exemplary embodiment, the aqueous phase fluid is supplied to the nozzle (10) at a flow rate of 2.8 ml/hr.

As previously mentioned, a wide variety of amphiphiles may be used in connection with the general inventive concepts described herein. In certain embodiments of the general inventive concepts, the amphiphile is an amphiphilic block copolymer. In certain other embodiments of the general inventive concepts, the amphiphile is a peptide amphiphile. Suitable amphiphilic block copolymers include, but are not limited to, poly(styrene-b-ethylene glycol), poly(ε-caprolactone-b-ethylene glycol), poly(ethylene glycol-b-distearoyl phophatidylethanolamine), and combinations thereof. Suitable peptide amphiphiles include, but are not limited to, palmitoyl-VVAAEE-NH2, palmitoyl-VVAAEEGIKVAV-COOH, palmitoyl-VVAAEEEEGIK-VAV-COOH, and combinations thereof. Those of skill in the art will appreciate that various other amphiphiles may be utilized and are within the scope of the general inventive concepts contemplated herein.

In certain embodiments of the method for producing polymeric nanoparticles, the amphiphile is supplied to the nozzle in the organic phase fluid. For example, in certain embodiments, the amphiphile is dispersed, dissolved, or otherwise added to the organic phase fluid. In certain other embodiments of the method for producing polymeric nanoparticles, the amphiphile is supplied directly to the nozzle. For example, the amphiphile can be supplied directly to the nozzle via gravity feed or mechanical means, such as a pump, or syringe pump. In certain other embodiments of the method for producing polymeric nanoparticles, the amphiphile is supplied to the nozzle in the aqueous phase fluid. For example, in certain embodiments, the amphiphile is dispersed, dissolved, or otherwise added to the aqueous phase fluid.

A wide variety of polymers may be utilized in the method for producing polymeric nanoparticles according to the general inventive concepts described herein. In certain embodiments, the polymer is supplied directly to the nozzle via gravity feed or mechanical means, such as a pump, or syringe pump. In certain embodiments, the polymer is a hydrophobic polymer. A wide variety of hydrophobic polymers may be utilized in accordance with the general inventive concepts. In certain embodiments, the hydrophobic polymer is biocompatible and biodegradable. For example, in one exemplary embodiment, the hydrophobic polymer is poly(lactic-co-glycolic acid). However, other hydrophobic polymers are contemplated in accordance with the general inventive concepts including, but not limited to, poly(lactic-co-glycolic acid), poly(lactic acid), poly(glycolic acid), poly (caprolactone), poly(ethylene glycol), and combinations thereof. In certain embodiments, the hydrophobic polymer is supplied to the nozzle in the organic phase fluid. For instance, the hydrophobic polymer is dispersed, dissolved, or otherwise added to the organic phase fluid.

In other embodiments, the polymer is a hydrophilic polymer. A wide variety of hydrophilic polymers may be utilized in accordance with the general inventive concepts described herein. For example, suitable hydrophilic polymers include, but are not limited to, acrylates, methacrylates, poly(ethylene oxide), cellulose ethers. Many other hydrophilic polymers are known to those of skill in the art and are contemplated herein. In certain embodiments, the hydrophilic polymer is supplied to the nozzle in the aqueous phase fluid. For example, the hydrophilic polymer is dispersed, dissolved, or otherwise added to the aqueous phase fluid.

As mentioned, an electric field is generated proximate the nozzle (10), particularly at a tip of the nozzle (10) where the fluid comprising the organic phase fluid, the aqueous phase fluid, the amphiphile, and the polymer exits. In certain embodiments, an electric potential is applied to the nozzle (10) and an electric potential is applied to a grounded electrode (20) to generate the electric field proximate the nozzle (10). The electric field causes the fluid exiting the nozzle (10) to form a cone-jet that disperses into a plurality of droplets. In effect, the electric field exerts a force on the fluid exiting the nozzle (10) and deforms the meniscus of the fluid. As previously described, when the electric field is high enough, it will exert a force that is greater than a limit based on the surface tension of the fluid such that the meniscus adopts a cone shape with a thin jet of the fluid. The thin jet then breaks up into a plurality of droplets of the fluid.

In certain embodiments of the general inventive concepts described herein, the electric field is generated by a power supply used to create an electric potential between the coaxial nozzle (10) and the grounded electrode (20), which may be a ring formed of copper or other conductive metals. In one exemplary embodiment, the grounded electrode (20) is positioned 0.5 cm below the tip of the coaxial nozzle (10). In certain exemplary embodiments of the method for producing polymeric nanoparticles, the electric field that is generated has an electric field strength within a range of about 3 kV/cm to about 35 kV/cm. In one exemplary embodiment of the method for producing polymeric nanoparticles, the electric field that is generated has an electric field strength within a range of about 6 kV/cm to about 7 kV/cm.

As the plurality of droplets is formed from the dispersion of the cone-jet, the plurality of droplets are collected. In certain embodiments of the method for producing polymeric nanoparticles, the plurality of droplets are collected in a collection solution. In an exemplary embodiment, the collection solution comprises an aqueous collection solution. For example, in certain embodiments, the aqueous collection solution comprises distilled water or double distilled water. In certain other embodiments according to the general inventive concepts described herein, the aqueous collection solution comprises ammonium acetate buffer. However, other types of aqueous solutions may be utilized and are contemplated by the general inventive concepts disclosed herein.

In one exemplary embodiment, the collection solution comprises an organic collection solution. For example, in certain embodiments, the organic collection solution comprises an alcohol, while in other embodiments, the organic collection solution comprises toluene. Those of skill in the art will appreciate that various other organic solutions may utilized in accordance with the general inventive concepts described herein.

In certain embodiments of the method for producing polymeric nanoparticles, the plurality of droplets are dispersed into a collector (30) containing the collection solution. The collector (30) may be a metal container, such as an aluminum dish, for example. In other embodiments of the method for producing polymeric nanoparticles, the plurality of droplets are dispersed directly into a collection solution without being exposed to the air, such as by submerging the nozzle in the collection solution.

In one exemplary embodiment of the method for producing polymeric nanoparticles, the plurality of droplets is collected on a surface. In other words, the plurality of droplets are dispersed directly onto a surface. Virtually any surface may be utilized to collect the plurality of droplets. For example, the plurality of droplets can be collected on a metal plate (e.g., aluminum plate), a transmission electron microscopy grid, or virtually any other type of surface.

In certain embodiments of a method for producing polymeric nanoparticles, after the plurality of droplets enters the collection solution, polymeric nanoparticles self-assemble in the collection solution. In one exemplary embodiment of a method for producing polymeric nanoparticles, the polymeric nanoparticles comprise a self-assembled structure enacpsulating particles of the polymer. For example, the self-assembled structure can comprise a micelle, or virtually any other self-assembling structure. The self-assembly is driven by interfacial instability. For example, in one embodiment, the amphiphiles orient to form a self-assembled structure having a hydrophilic shell and a hydrophobic core. In essence, the self-assembled structure forms a particular sized "template," which can be used to control the size and shape of the polymeric nanoparticles formed. During the formation of the self-assembled structure, the particles of hydrophobic polymer present are attracted to the hydrophobic segments of the amphiphiles such that as the self-assembled structures are forming, particles of the hydrophobic polymer are drawn to and encapsulated within the hydrophobic core of the self-assembled structure. Because the self-assembly process is spontaneous, and because the self-assembled structures are thermodynamically stable, ultrasmall polymeric nanoparticles (<100 nm) can be created in a robust and reproducible process.

In certain embodiments of the method for producing polymeric nanoparticles, when the plurality of droplets is collected on a surface, polymeric nanoparticles self-assemble on the surface. In one exemplary embodiment, the polymeric nanoparticles comprise a self-assembled structure encapsulating the polymer. As mentioned above, the self-assembled structure can comprise a micelle, or other types of self-assembling structures. In this particular embodiment, the driving force for the self-assembly of the nanocomposite particles is provided by an organic phase-aqueous phase interface present in the plurality of droplets. In addition, self-assembly may be driven as the organic solvent is removed, such as by evaporation or diffusion.

In one exemplary embodiment according to the general inventive concepts contemplated herein, a method for producing polymeric nanoparticles employs a batch process. In one exemplary embodiment, an amphiphile and a polymer is added to a suitable solvent to form an amphiphile-polymer-solvent mixture. The amphiphile-polymer-solvent mixture is introduced to an aqueous solution. The amphiphile-polymer-solvent mixture and the aqueous solution are mixed to form an oil-in-water emulsion. The solvent is removed from the oil-in-water emulsion to produce the polymeric nanoparticles. For example, in one embodiment, as the solvent is removed (e.g., through evaporation or diffusion), the amphiphiles orient to form a self-assembled structure having a hydrophilic shell and a hydrophobic core. In essence, the self-assembled structure forms a particular sized "template," which can be used to control the size and shape of the polymeric nanoparticles formed. During the formation of the self-assembled structure, the particles of hydrophobic polymer present are attracted to the hydrophobic segments of the amphiphiles such that as the self-assembled structures are forming, particles of the hydrophobic polymer are drawn to and encapsulated within the hydrophobic core of the self-assembled structure, the amphiphile forms self-assembled structures that encapsulate particles of the polymer to form the polymeric nanoparticles. Any number of the amphiphiles, polymers, solvents, and aqueous systems previously disclosed may be utilized in connection with this exemplary embodiment.

EXAMPLES

The following examples illustrate exemplary embodiments or features of the general inventive concepts described herein. The examples are given solely for the purpose of illustration and are not to be construed as limitations of the general inventive concepts, as many variations thereof are possible without departing from the spirit and scope of the general inventive concepts.

Example 1

Example 1 illustrates an exemplary embodiment of a nanocomposite particle (CNP), an exemplary method of producing the CNPs, and exemplary methods of using the CNPs according to the general inventive concepts described herein.

Materials and Methods

Chemicals—Poly(styrene-b-ethylene glycol) with molecular weight 3800-b-6500 (Dalton) was purchased from Polymer Source. Quantum dots (QDs) with hydrophobic surfaces ($\lambda_{em}$=545 nm, 10 pmol for green QDs, and $\lambda_{em}$=605 nm, 2 pmol for red QDs) were purchased from Invitrogen. Chloroform and poly(vinyl alcohol) (13,000-23,000 Dalton, 87-89% hydrolyzed) were purchased from Aldrich. Dulbecco's modified Eagle's medium and fetal bovine serum for culturing NIH3T3 cells were purchased from ATCC.

Preparation of CNPs—CNPs were prepared by thoroughly mixing green QDs ($\lambda_{em}$=545 nm, 10 pmol), red QDs ($\lambda_{em}$=605 nm, 2 pmol) and polymer (50 pmol) in chloroform (100 µl). The mixture was then added to an aqueous solution of poly(vinyl alcohol) (5 mg/ml) at a volume ratio of 1:5 (oil:water). After vortexing for 1 min, the emulsion formed was quickly mixed with deionized water (volume ratio of emulsion to water 1:5). The emulsion droplets were permitted to settle, and were then transferred to an open container for rapid evaporation of chloroform. The milky emulsion droplets became transparent after chloroform removal, indicating the formation of CNPs. CNPs were filtered through a syringe filter with 0.22 µm pore size (Millipore) to eliminate large aggregates.

Transmission Electron Microscopy (TEM)—CNPs were negatively stained with 1% phosphotungstic acid (PTA). TEM studies were conducted using an FEI Tecnai G2 Spirit Transmission Electron Microscope (80 kV). QDs and PTA are electron dense and appear dark, whereas the shells of micelles appear light in the images.

Fluorescent Microscopy and Image Analysis—To uniformly disperse CNPs on a coverslip surface, CNP solution (10 µl, 1-10 nM) was sandwiched between two coverslips and placed in a fume hood for 10 minutes. The two coverslips were then separated and exposed to ambient conditions for another 10 minutes. Coverslips were then secured to microscopy slides for fluorescent microscopy observation. CNPs were imaged with an Olympus BX41 microscope (100× oil immersion objective) equipped with a 100W mercury lamp (Chiu Technical Corporation, $\lambda_{ex}$=488 nm. Fluorescent emission was filtered through a long-pass filter and collected by an Olympus DP70 CCD camera. Image analysis was conducted using Image J image analysis software. Fluorescent intensity of a pixel was determined by its gray level. Fluorescent intensity of a particle was determined by multiplying the mean gray level of all pixels of the particle by the area (number of pixels) occupied by the particle. A trajectory of a particle was identified by manually linking the particle centroids on all frames of a time series. Movement of different particles through the focal plane was imaged by manually adjusting the microscope stage. Camera exposure time used was 500 ms for QD blinking and CNP alternating color images, 16.7 ms for QD aggregates, and 0.8 ms for the CNP aggregates.

Estimation of FRET Efficiency Between QDs—The FRET efficiency between the two QD sizes used were estimated as follows:

$$R_0 = \left(\frac{9000(\ln 10)\kappa^2 Q_D}{128\pi^5 N n^4} \times I\right)^{\frac{1}{6}} \approx 3.9 \text{ nm} \quad (1)$$

where $R_0$=Förster distance, I=spectral overlap function=$2.2309 \times 10^{15}$ (obtained by integrating the area under the overlap area of donor QD and acceptor QD), $\kappa^2$=orientation factor=2/e, $Q_D$=donor quantum yield=80% (as per QD manufacturer0, N=Avogardo's number=$6.02 \times 10^{23}$, and n=refractive index=2.2 (average of refractive index of CdSe and polystyrene).

$$E = \frac{R_0^6}{R_0^6 + r^6} \quad (2)$$

where E=FRET efficiency and r=distance between centers of QD FRET pair.

Assuming a zero separation between the two QDs (i.e., two QDs touching each other), the distance between FRET donor and acceptor is the sum of the radii of the two QDs. The QD radii as measured by TEM are: $r=r_1+r_2=2.05+3.45=5.48$ nm; thus, E=13.1%, and with 1 nm separation between two QDs, E=5.2%.

Results and Discussion

Figure 4:
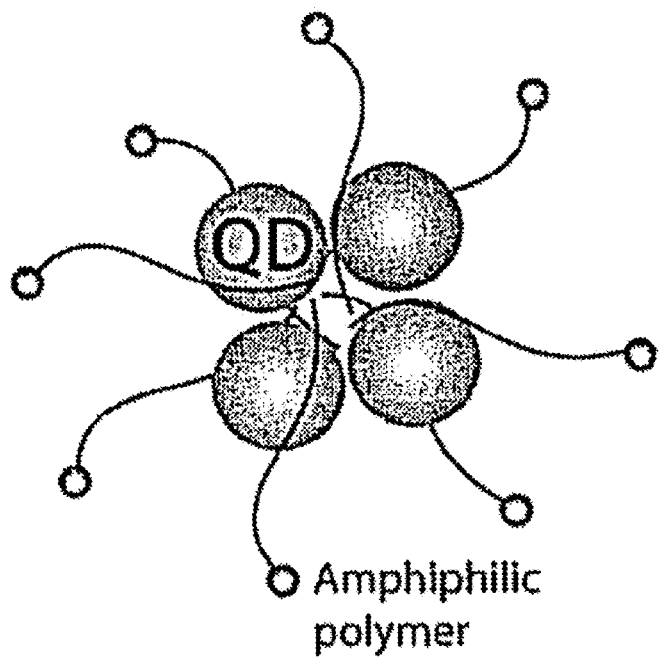
FIG. 4 shows a schematic of an exemplary nanocomposite particle (CNP) comprising quantum dots formed via micelle encapsulation.

CNPs were formed by coencapsulation of quantum dots (QDs) with differing emission wavelengths (Invitrogen, $\lambda_{em}$=545 nm and 605 nm for green and red QDs, respectively) in polymeric poly(styrene-b-ethylene oxide) (MW 3800-b-6500) micelles. Co-encapsulation was achieved using the interfacial instability process in which oil-in-water emulsion droplets were transformed into micelles (~25 nm in diameter) upon evaporation of the oil phase (e.g., chloroform). Because the oil phase contained QDs with differing emission wavelengths and amphiphilic polymers, the resultant micelles comprised polymer shells with QDs isolated in the micelle core (FIG. 4). Exact numbers of red and green QDs in each micelle are difficult to determine from transmission electron microscopy (TEM) as QDs within the 3D micelle overlap when projected onto a 2D image.

Figure 5:
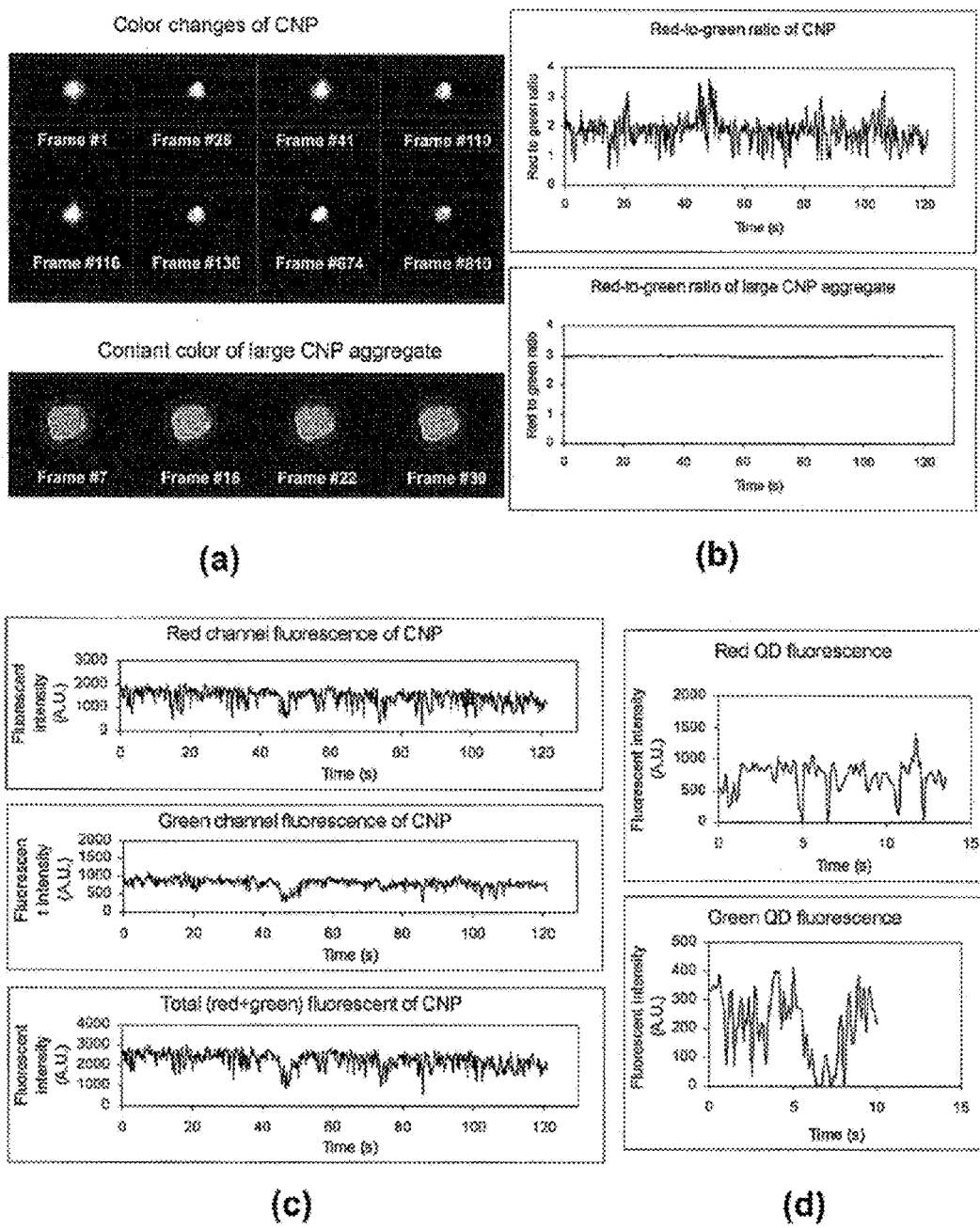
FIG. 5 illustrates exemplary nanocomposite particle (CNP) dynamics of (a) fluorescence, (b) red-to-green ratio, and (c) intensities. (d) illustrates the fluorescence intensity of a single red quantum dot and a single green quantum dot.

CNP suitability for particle tracking applications was assessed using a fluorescent microscope ($\lambda_{excitation}$=488 nm), CCD camera, and long-pass filter to permit simultaneous green and red channel observation. The CNPs exhibit multiple, alternating fluorescence emission colors, including those of the constituent green and red QDs and their combination (FIG. 5a). The ratio of fluorescence in the CNP red channel to that of the green channel (R/G ratio) changed throughout the observation period (0.564-3.662 AU, or 550% difference, FIG. 5b), leading to a continuous change in fluorescent color (FIG. 5a). The change in R/G ratio was abrupt; indicating an abrupt color change between red (high R/G ratio), yellow/orange (medium R/G ratio), and green (low R/G ratio). Additionally, the fluorescent colors of smaller regions within the CNP also changed continuously and abruptly. For example, in frame 41 (5.453 s), the CNP appears as a large orange core surrounded by a thin red shell (R/G ratio=1.846), whereas in frame 110 (14.497 s) the CNP appears green (R/G ratio=0.580). The nonuniform color distribution in the CNP indicates a heterogeneous distribution of differently colored QDs in the CNP. In contrast, a large aggregate of CNPs (obtained from the visible precipitate of an unfiltered CNP solution after 1 week of storage) exhibited near-constant fluorescent color and R/G ratio (2.931-3.004 AU, or 2.4% difference). Therefore, the alternating-color feature of the CNP can serve as a marker of single (or small cluster) status.

To evaluate the dynamics of fluorescence intensity, overall CNP fluorescence intensity and that of individual red and green channels were compared with the intensity of separately imaged single green and red QDs (FIGS. 5c and 5d). Over an observation period of 2 min, the total CNP fluorescence intensity remains high (ranging from 588.07 to 2995.998 AU), although at several time points the fluorescent intensities of individual CNP color channels were diminished as a result of constituent QD blinking (FIG. 5c). Compared to individual QDs, for which fluorescence was nearly extinguished at several time points (FIG. 5d, green QD, 0-408.000 AU; red QD, 13.988-1429.012 AU), CNP fluorescence was virtually continuous. Additionally, CNPs are much brighter than constituent QDs, which will significantly improve signal-to-noise ratio in tracking studies.

These measurements can also be used to estimate the number of constituent QDs in a CNP, which is important for potential mulitplexing applications. If numbers of individual constituent QDs can be determined in situ, it would be possible to construct CNPs with known red to green particle ratios, which could then be used to track different species. From comparison of fluorescence intensity in CNP channels (FIG. 5c) to that of single QDs (FIG. 5d) (integrated over 10 s to compensate for blinking), it is estimated that the CNP shown in (FIG. 5) contains four (i.e., 4.09) green QDs and two (i.e., 2.24) red QDs. However, given the spectral overlap and close proximity between QDs with a CNP, Förster resonance energy transfer (FRET) could occur. Thus, the FRET efficiency between green and red QDs was calculated and determined to be low (13.1% for 0 nm and 5.2% for 1 nm separation). The low FRET efficiency observed in QD-QD pairs relative to molecular FRET donor/acceptors results from the large size of QDs. These calculations indicate that FRET does not significantly interfere with the fluorescent properties of the CNPs.

Figure 6:
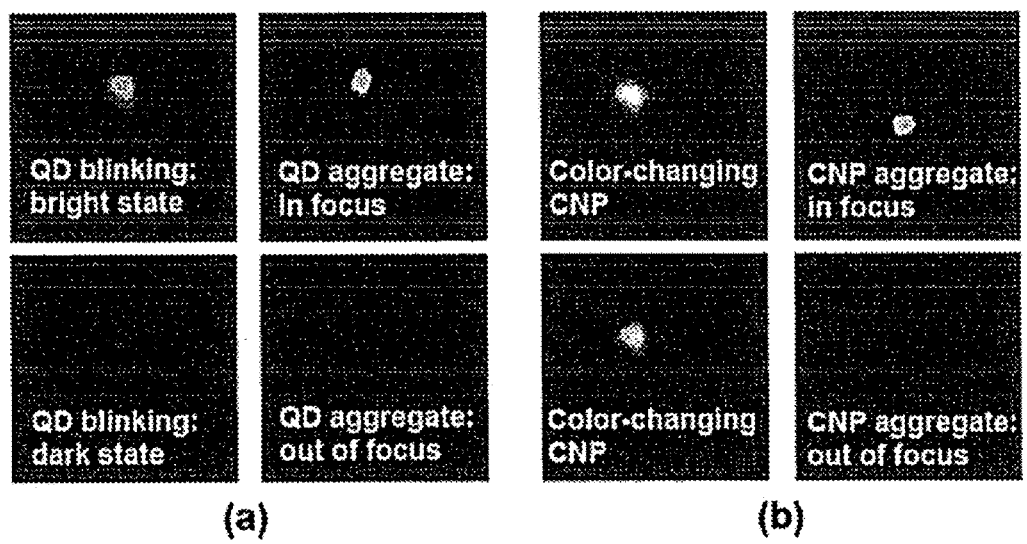
FIG. 6 illustrates (a) that quantum dot blinking is not distinguishable from quantum dot aggregates drifting outside the focal plane, whereas (b) illustrates exemplary nanocomposite particles (CNP) color changes are distinguishable from CNP aggregates exiting the focal plane.

In addition to permitting near continuous tracking and confirmation of aggregation status, the alternating-color fluorescence emission can be used to solve another longstanding problem in QD-based particle tracking: discrimination of out-of-focus large aggregates from single (or small clusters of) nanoparticles. In highly dynamic systems using conventional QDs, rapid 3D motion out of the focal plane cannot be distinguished from blinking because both lead to disappearance of the fluorescence signal (FIG. 6a). In contrast, CNPs permit facile and unambiguous confirmation of aggregation status because (1) CNPs produce alternating-color fluorescence emission and (2) the constituent QDs in a CNP move as an ensemble. Thus, a CNP aggregate completely moving out of focus manifests as a complete loss of fluorescence, which is clearly distinguishable from the alternating-color signal of a single (or small cluster of) CNP (FIG. 6b).

Figure 7:
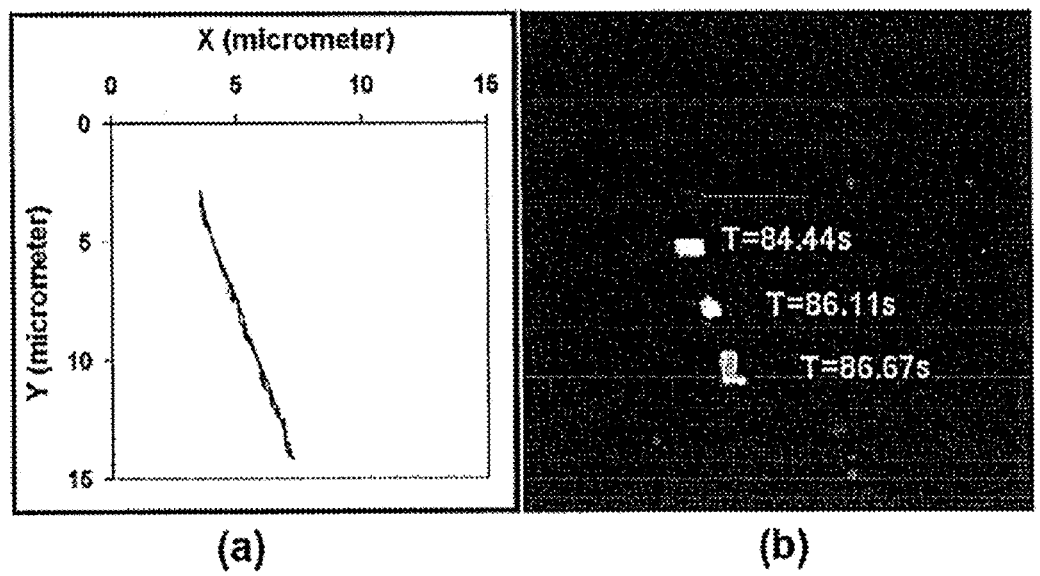
FIG. 7 illustrates dynamic tracking of an exemplary nanocomposite particle (CNP). (a) shows CNP trajectory; and (b) shows a superimposed image of the CNP at several time frames of a jump (fast and large location change)

Drop-cast CNPs were moved by manual control of the microscope stage. A typical CNP was tracked continuously for 2 min, much longer than the reported duration between blinking interruptions for any single QD-trajectory reported in the literature (FIG. 7a). The CNP moved throughout the field of view while exhibiting continuous and abrupt color changes, indicating single (or small cluster) status. CNP alternating-color fluorescence is distinguishable from potential fluorescent intensity and color changes that may result from particle growth (e.g., by Ostwald ripening) and aggregation. It has been reported that the fluorescence intensity of some large QD aggregates (e.g., QDs with poorly protected surfaces) experience a significant, but gradual, decay before reaching steady state under certain experimental conditions. However, large CNP aggregates, which comprise commercially available QDs with well-protected surfaces, emit constant fluorescence in all color channels under all experimental conditions tested. Additionally, even if particles with poorly protected surfaces were used, because the initial decay of fluorescence would be gradual, any possible alteration of fluorescence would also be gradual and could thus be distinguished from the abrupt color changes exhibited by single (or small cluster of) CNPs.

There were several fast and large location changes ("jumps") in the trajectory (e.g., from 84.44 to 87.22 s). In particular, a color-changing event coincided with the jump event between 84.44 and 86.67 s (FIG. 7b). The color-changing event indicates that during this time at least one constituent QD in the CNP was blinking, which highlights the benefit of using a CNP rather than a QD for tracking If this constituent blinking QD alone were used as a tracer particle, the trajectory after the "jump" would be lost due to the coincidence of the blinking and the jump. Alternatively, "nonblinking QDs" in which blinking is reduces or eliminated by mediators/compensators on the QD surface, coating QDs with a thick shell, or synthesizing QDs with a gradually changing potential energy function could be used. However, these would not permit aggregation status (or lack thereof) to be confirmed, since blinking would be absent, electron microscopy and single photon counting could not be applied in situ, and the fluorescent particle spot size can vary with camera exposure time and is subject to the diffraction limit (i.e., not the actual size of the particle).

In addition to the optical properties, CNPs have several features that make them particularly useful for particle tracking studies. First, about 20% of the as-synthesized CNPs, without separation or optimization, show near-continuous fluorescence, alternating-color properties (with the remainder providing typical single color fluorescence). Second, yields can be enhanced by fluorescence sorting (e.g., FACS); however, CNPs can also be used as-synthesized with investigators selectively tracking those fluorescent particles with the alternating-color feature. Third, CNPs are small and are therefore not expected to interfere with most processes being tracked. Further, bioconjugation of CNPs can be accomplished by well-documented procedures (using amphiphilic polymers with —COOH or —NH$_2$ end groups). In addition, CNPs are stable in the biological environments commonly used for particle tracking studies. For example, after 12 h in cell culture medium (Dulbecco's modified Eagle's medium, containing 10% serum, 37° C.), CNPs were free of significant aggregation and their near-continuous fluorescence and alternating-color properties were preserved. Cell culture medium, blood, or cytoplasm can all potentially interact with the QD surface through oxidation/reduction reactions or molecular absorption to alter QD properties. The high tolerance for biological environments displayed by CNPs should at least partially result from protection of the QD surface by the micelle.

The properties of the CNPs can significantly enhance dynamic particle tracking in fluids (e.g., biological environments or microfluidic flows). However, it is contemplated that CNPs can be used for magnetic manipulation and multimodal imaging, or for use in creating multiplexed particles that can track multiple biomolecules or nanomaterials simultaneously. In addition, CNPs may also serve as a platform for investigating energy transfer and electronic coupling of QDs in a controlled microenvironment.

Example 2

Example 2 illustrates an exemplary embodiment of a method for producing nanocomposite particle according to the general inventive concepts described herein.

Materials and Methods

Electrospray Synthesis of Nanocomposite Particles—The process of electrospray production of nanocomposite particles includes preparing the electrospray solutions, generating a compound droplet via coaxial electrospray, collecting the aerosol droplets in an aqueous solution yielding a microemulsion, and allowing the microemulsion to form micelles through the interfacial instability effect.

First, superparamagnetic iron oxide nanoparticles (SPION), quantum dots (QDs), and poly(styrene-b-ethylene glycol) (PS-PEG) were separately suspended in chloroform. Then, an organic phase was prepared by mixing SPION (1 mg/ml Fe, 225 µl), QDs (0.1 µM, 450 µl), and PS-PEG (10 mg/ml, 90 µl). The organic phase was delivered to the inner stainless steel capillary of a coaxial needle at a flow rate of 0.48 ml/hr using a syringe pump. An aqueous phase was prepared by dissolving poly(vinyl alcohol) in double distilled water at 5 mg/ml. The aqueous phase was delivered to the outer annulus of the coaxial needle at a flow rate of 2.8 ml/hr using a second syringe pump. After allowing both flow rates to stabilize, compound droplets, with an organic core and aqueous shell, could be observed dripping from the coaxial needle using a high performance camera and monitor. When both flow rates stabilized, a power supply was used to apply a positive high voltage to the coaxial needle with respect to a grounded copper ring positioned 0.5 cm below the needle tip. At a voltage of 6-7 kV, a concave cone-jet was observed at the tip of the coaxial needle. An aluminum dish containing 14 ml of aqueous phase (either double distilled water, or ammonium acetate buffer) was placed 10 cm below the nozzle tip to collect the aerosol droplets. After one hour of collection, a red-brown emulsion was visible in the bottom of the collection dish. This was transferred to a 15 ml centrifuge tube. After 2 hours, this emulsion vanished leaving a transparent suspension of nanocomposite particles.

Dynamic Light Scattering: Hydrodynamic Particle Size Distribution—The hydrodynamic particle size of the nanocomposite particles was characterized using dynamic light scattering equipment (Brookhaven Instruments Corporation, BI 200SM). Samples were taken from the resulting suspension and diluted with distilled water if necessary to reduce the intensity of scattered light to the acceptable range of the instrument (between 10 and 200 kCPS). The wavelength of the laser was 633 nm, the pinhole was set to 200, and the detection angle was 90°. A measurement lasted 2 minutes and mean particle size weighted by volume ($D_{p,mean,v}$) was recorded. The average and standard deviation of five successive measurements was reported.

Scanning Mobility Particle Size (SMPS) Distribution—The electrical mobility of aerosolized particles was characterized using a Scanning Mobility Particle Sizing Spectrometer (SMPS, TSI 3936). The compound electrospray droplets were collected, and the micelle suspension was formed in ammonium acetate buffer. A small sample of this suspension was aeosolized using a commercial electrospray aerosol generator (TSI 3040). The aerosol was classified by electrical mobility using an electrostatic classifier (TSI 3080) with a differential mobility analyzer (DMA, TSI 3081). The particles were then quantified using an ultrafine water condensation particle counter (UWCPC, TSI 3786). The equipment was programmed to scan through a range of electrical mobility particle sizes from 9 nm to 400 nm counting the particles at each size. Thus, a distribution of electrical mobility particle size was constructed and plotted on log-log axis.

Transmission Electron Microscopy—Images of the resulting micelles in the transparent suspension were obtained using a FEI Tecnai G2 Bio Twin TEM. First, 10 µl droplets of samples were pipetted onto a clean silicone pad. Micelles were loaded onto formvar/carbon-coated nickel grids by placing the grid over the sample droplet with the support film facing down. Micelles were allowed to collect on the support film for 2 minutes, after which time the excess liquid was wicked away using filter paper. Next, the grid was placed over a 10 µl droplet of phophotungstic acid (PTA, 1%). Negative staining with 1% PTA was allowed for 2 minutes and the excess liquid was wicked away. The grid was then imaged.

Particle Tracking with Fluorescence Microscopy in the Presence of a Neodymium Magnet—The fluorescent and magnetic functions of the particles generated by electrospray were simultaneously tested by viewing a particle sample under fluorescence microscopy in the presence of a neodymium magnetic needle. The filter of the microscope was set to the emission wavelength of the quantum dots and a glass dish with a small cylindrical segment of neodymium magnetic needle was placed on the stage. A 10 µl sample was pipetted onto the glass dish immersing the magnet in the sample. A video was recorded to investigate whether or not fluorescent particles could be observed moving toward the magnet. The video was processed using Image J software.

Results and Discussion

Micelles were synthesized using the experimental setup illustrated in FIG. 1. The organic mixture comprising the solvent (chloroform), polymer poly(styrene-b-ethylene glycol), SPIONs, and QDs, flowed through the central needle while a polyvinyl alcohol-water mixture flowed through the outer needle. The flow rates and voltages were adjusted to achieve a stable cone-jet. Aerosol droplets were collected in a collection dish containing distilled water. In the absence of stirring, a reddish-brown emulsion segregates to the bottom of the aluminum collection dish. However, the emulsion is capable of being dispersed with gentle agitation. After 2-3 hours post spraying, a clear solution results. The disappearance of the reddish-brown emulsion after time and gentle agitation indicates the formation of micelles via the interfacial instability effect. Thus, the electrospray process forms the emulsion in a continuous, automated fashion.

Figure 8:
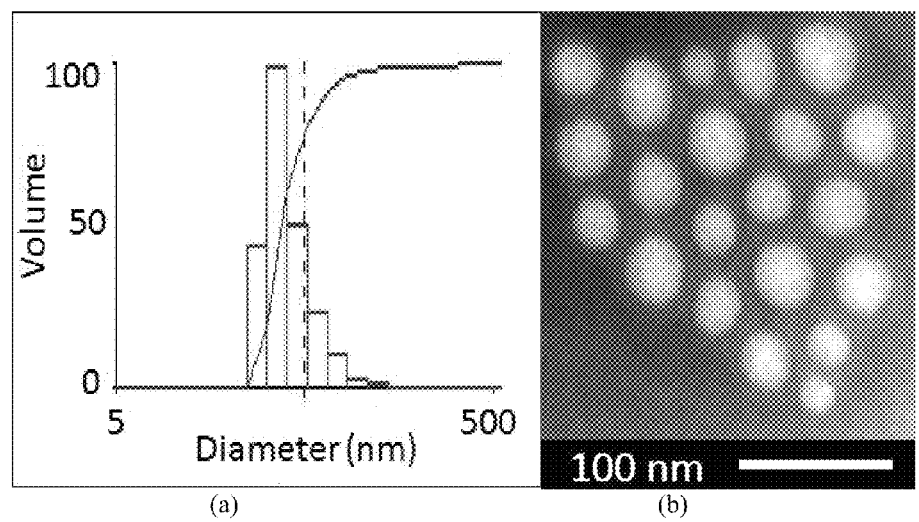
FIG. 8 illustrates (a) nanocomposite particle size distribution as measured with Dynamic Light Scattering; and (b) TEM images of nanocomposite particles comprising quantum dots and superparamagnetic iron oxide nanoparticles.

After the emulsion vanished and the solution became transparent, a sample was removed and analyzed using DLS. A sample particle size distribution is illustrated in FIG. 8a and is unimodal. Based on 5 measurements, the mean particle diameter, weighted by volume, was 44±7 nm. The same solution was then imaged using TEM, and FIG. 8b illustrates that the micelles containing both SPIONs and QDs have diameters between 30 nm and 40 nm, values that agree well with the dynamic light scattering data.

Since the particles contain QDs, the random motion of particles in solution, observed under a fluorescent microscope, can also be used to determine particle size. A 10 μl drop was placed in a glass dish and the filter of the microscope was set to the fluorescence wavelength of the quantum dots. (FIG. 5 of the paper) illustrates the trajectory of three such particles. The mean square displacement $\langle x^2 \rangle$ of the particle is related to the diffusion of the particle D and time t by $$\langle x^2 \rangle = 4Dt. \quad (1)$$

Figure 9:
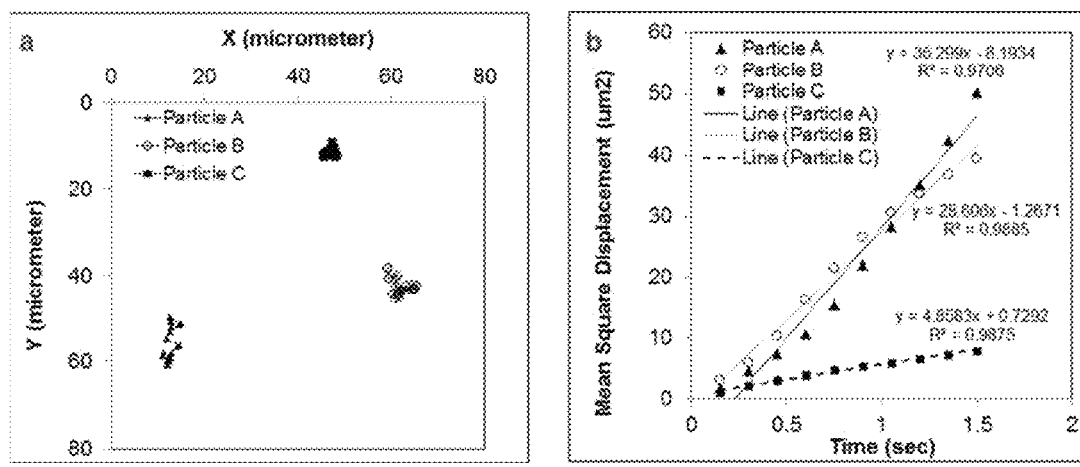
FIG. 9 illustrates (a) the trajectories of 3 particles; and (b) how the mean square displacement of the particles increases linearly with time.

The value of D is in turn related to the particle radius diameter $d_p$ through the Stokes-Einstein equation $$d_p = \frac{k_B T}{3\pi \mu D} \quad (2)$$

where $k_B$ is the Boltzmann constant, T is temperature, and μ is the viscosity of the surrounding medium. For the particles illustrated in FIG. 9, this method yielded particle radii of 54 nm and 68 nm. Significantly larger particles, d~400 nm, were also observed and are assumed to correspond to micellar aggregates.

Figure 10:
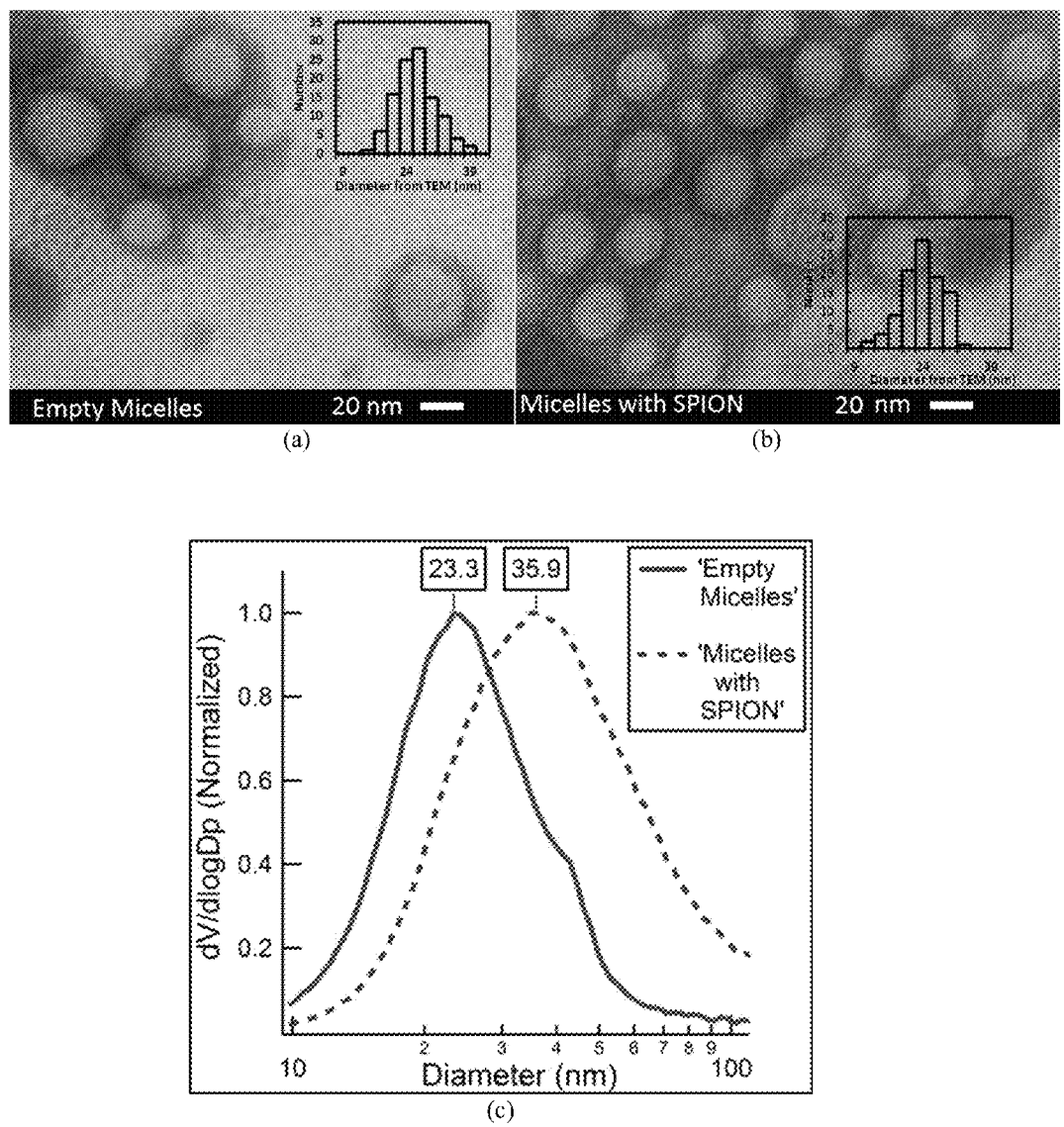
FIG. 10 illustrates TEM images of (a) empty micelles; (b) micelles loaded with superparamagnetic iron oxide nanoparticles (SPIONs); and (c) Scanning Mobility Particle Size (SMPS) Distribution of empty micelles and micelles loaded with SPIONs. Particle size distributions were measured from TEM images using Image J software and are shown in the insets of (a) and (b)

SPION and quantum dot encapsulation are difficult to quantify, since visible evidence of either component in the interior or the exterior of the micelles is rare. To illustrate that encapsulation efficiency is not rare, two samples of micelles were generated. In the first sample, only the PS-PEG block copolymer was included in the organic phase, in order to generate empty micelles. In the second sample, PS-PEG and SPION were included in the organic phase in order to generate SPION loaded micelles. TEM images of the samples are illustrated in FIGS. 10a and 10b. Again the micelles are approximately 30 to 40 nm in diameter, and there is no direct evidence for SPION encapsulation. To demonstrate that these miscelles do differ in a manner consistent with the inclusion of SPIONs, empty and loaded micelles were suspended in ammonium acetate buffer, resprayed using a TSI electrospray device, and the aerodynamic size distribution of the resulting aerosol was measured using a TSI Scanning Mobility Particle Sizer. At the low dilutions used here, droplets created by the electrospray contain at most one micelle. As illustrated in FIGS. 9a and 9b, the volume average aerodynamic diameters $d_a$ are comparable to the values determined by the other methods. The slightly smaller size is consistent with a dry micelle where the polymer is collapsed and more compact than in the hydrated state. Furthermore, the SPION loaded micelles have a distinctly higher aerodynamic diameter than the empty micelles. This can be explained by recognizing that the aerodynamic diameter is related to the physical diameter of the particle by: $d_a = d_p \rho^{1/2}$, where ρ is the particle density. There are at least three reasons why $d_a$ should increase with iron loading in the micelles. The first is an increase in the physical size due to the inclusion of iron nanoparticles, the second is an increase density of the iron oxide loaded micelle relative to the empty micelle, and finally, the presence of solid iron oxide particles may make the micelle more resistant to collapse as it dries.

Figure 11:
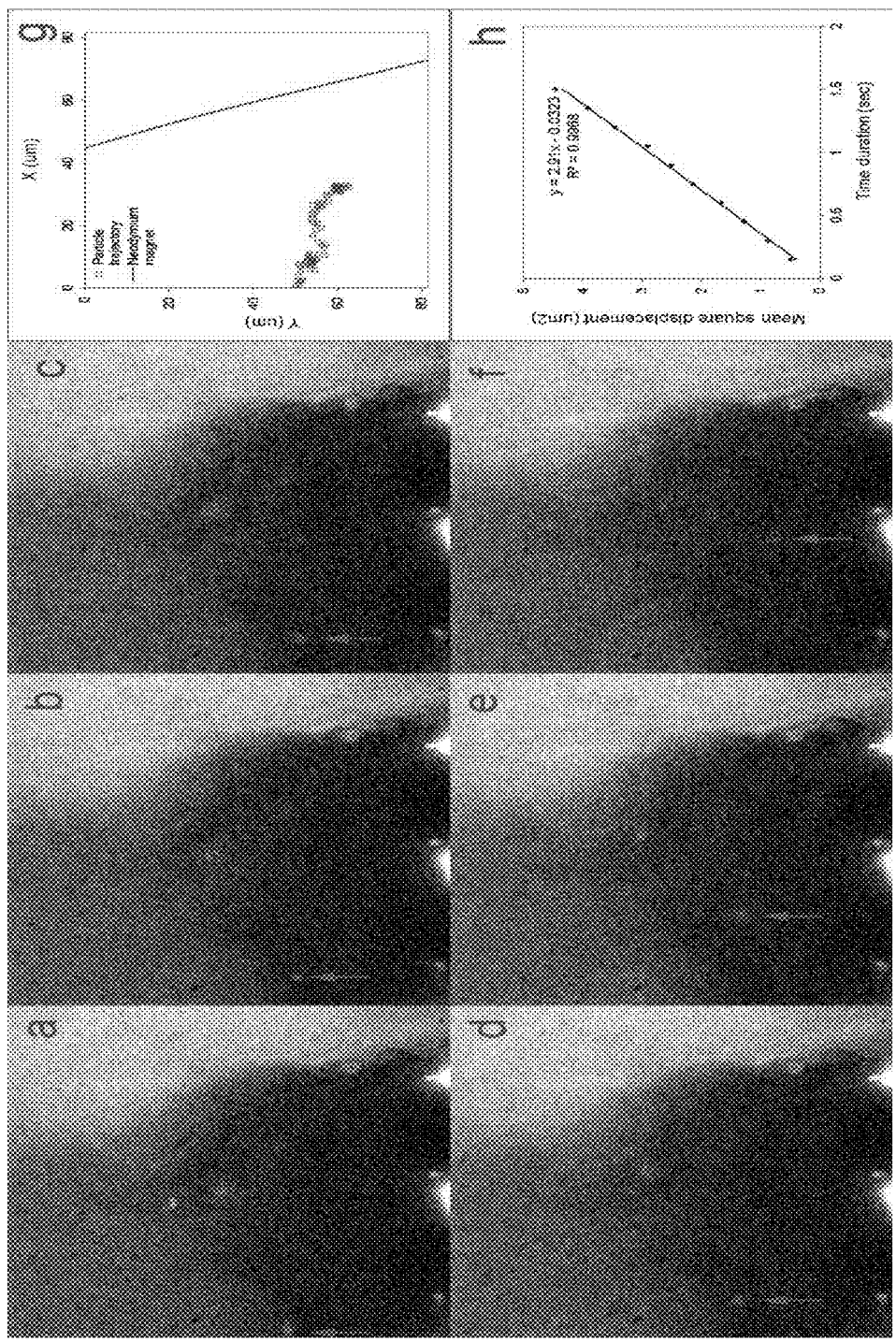
FIG. 11 illustrates in (a)-(f) a series of images that follow the movement of a fluorescing particle toward a magnetic needle, and demonstrates that the nanocomposite particles exhibit fluorescent and magnetic functionalities. (g) and (h) show the particle trajectory and mean square displacement, respectively.

Finally, to demonstrate that the nanoparticles formulated with both QDs and SPIONs had both fluorescent and magnetic functionalities, the nanocomposite particles were observed under a fluorescence microscope in the presence of a neodymium magnet. Migration of the fluorescent particles toward the magnetic needle indicated the co-localization of SPION and quantum dots, demonstrating they were co-encapsulated in the micelle. FIG. 11 (a)-(f) illustrates a series of images from a video recording showing a particular fluorescent particle as it migrates toward the magnet.

To estimate the size of the particle observed in FIG. 11, its motion in time was tracked and the results are illustrated in FIGS. 11g and 11h. The motion of this particle reflects both the directed motion due to the magnetic field and the random motion due to Brownnian diffusion. In a magnetic field, the velocity v of a particle is governed by $$v = \frac{M(B_0) d_p^2}{18\mu} \nabla B \quad (3)$$

where $M(B_0)$ is the magnetization of the particle and B is the magnetic field. Thus, in a region of constant ∇B, the velocity of the particle should be constant and perpendicular to the magnetic field lines. Near the magnet, ∇B is constant, and B is high enough to ensure $M(B_0)$ is constant. Thus, we can deconvolve the motion of the particle into its directed and fluctuating components. As illustrated in FIG. 11h, the mean square displacement from the directed motion is a linear function of time, and from the slope of the line and Eqs (1) and (2), the size of the micelle can be determined. In this case, $d_p = \sim 340$ nm, suggesting an aggregate. Assuming that each micelle in the aggregate has an average $d_p$ of 60 nm, the average value based on the earlier diffusion analysis, a volume balance suggest the aggregate contains ~180 micelles. Eqn (3) can now be used to determine $M(B_0)$ and, finally the number of SPIONS $N_S$ can be estimated using $$M(B_0) = N_S M_S V_S \quad (4)$$

where $M_S$, and $V_S$ are the mass and volume of a single SPION. In this case $N_S$ is 165 and each micelle contains on average 0.68 SPIONS. Although this is only an order of magnitude analysis, it suggests that most micelles contain an iron nanoparticle. The analysis also demonstrates that imaging studies of this sort are more sensitive to larger aggregates since single micelles move much more slowly ($v \propto d_p^2$) and tracking their motion on the time scale of a typical experiment is more difficult.

Example 3

Example 3 illustrates an exemplary embodiment of a method for producing polymeric nanoparticle according to the general inventive concepts described herein.

Figure 12:
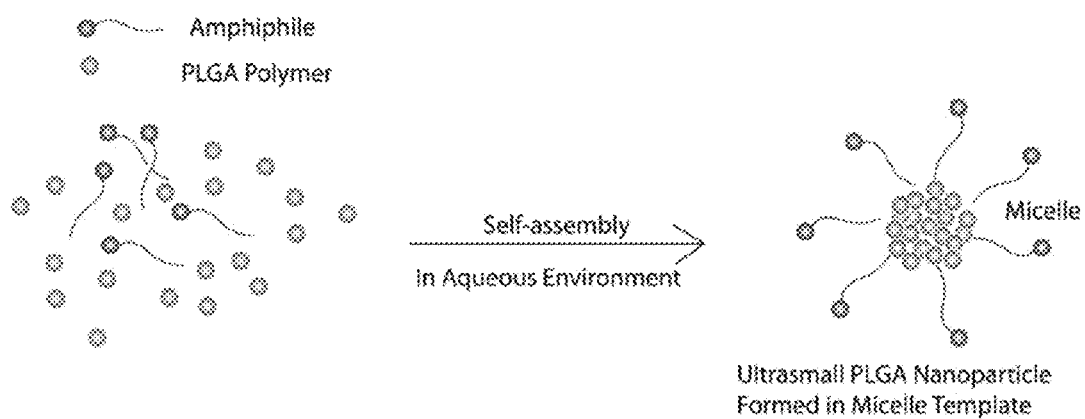
FIG. 12 schematically illustrates an exemplary embodiment of the formation of polymeric nanoparticles.

Polystyrene-co-polyethylene glycol (PS-PEG) was used as a template to form nanoparticles comprising poly(lactic-co-glycolic acid) (PLGA) via self-assembly. As shown in FIG. 12, PS-PEG is an amphiphile that that self-assembles to form micellar structures in water. PLGA (hydrophobic) spontaneously enters the hydrophobic core of the micelle template, resulting in PLGA particles whose sizes are primarily controlled by the template. Sizes can be extremely small (easily 40 nm and potentially as small as several nm with selected amphiphiles). In one procedure to form micelle-templated PLGA particles, PS-PEG and PLGA are dissolved in chloroform, which is then introduced into water. Vortexing the mixture gives an oil-in-water emulsion. Following evaporation of chloroform, the emulsion is transformed to a transparent solution of micelle-templated PLGA nanoparticles. In essence, the process produces "filled" micelles, that is, micelles that contain a polymer within its core.

Figure 13:
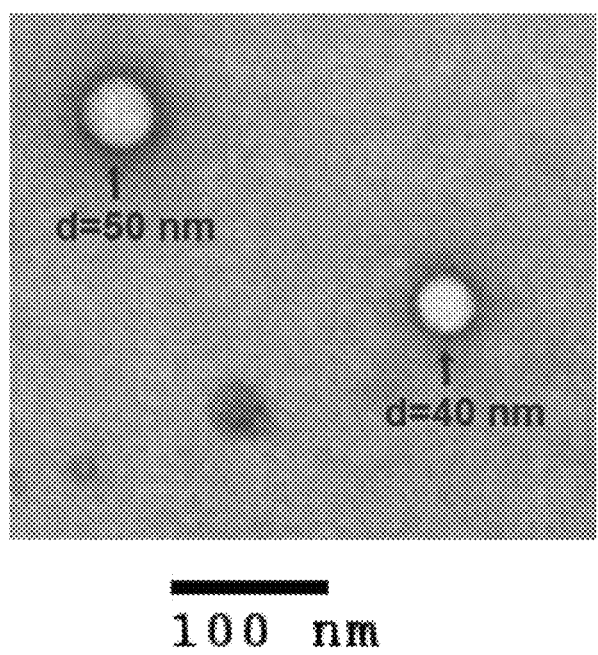
FIG. 13 shows a TEM image of exemplary polymeric nanoparticles.

FIG. 13 shows TEM images of PLGA particles produced using the self-assembly process. As can be clearly seen, particle size is ~40-50 nm, which is much smaller than 100 nm. By choosing different micelle-forming molecules (i.e., amphiphiles), the particle size of PLGA particles could be further reduced.

Figure 14:
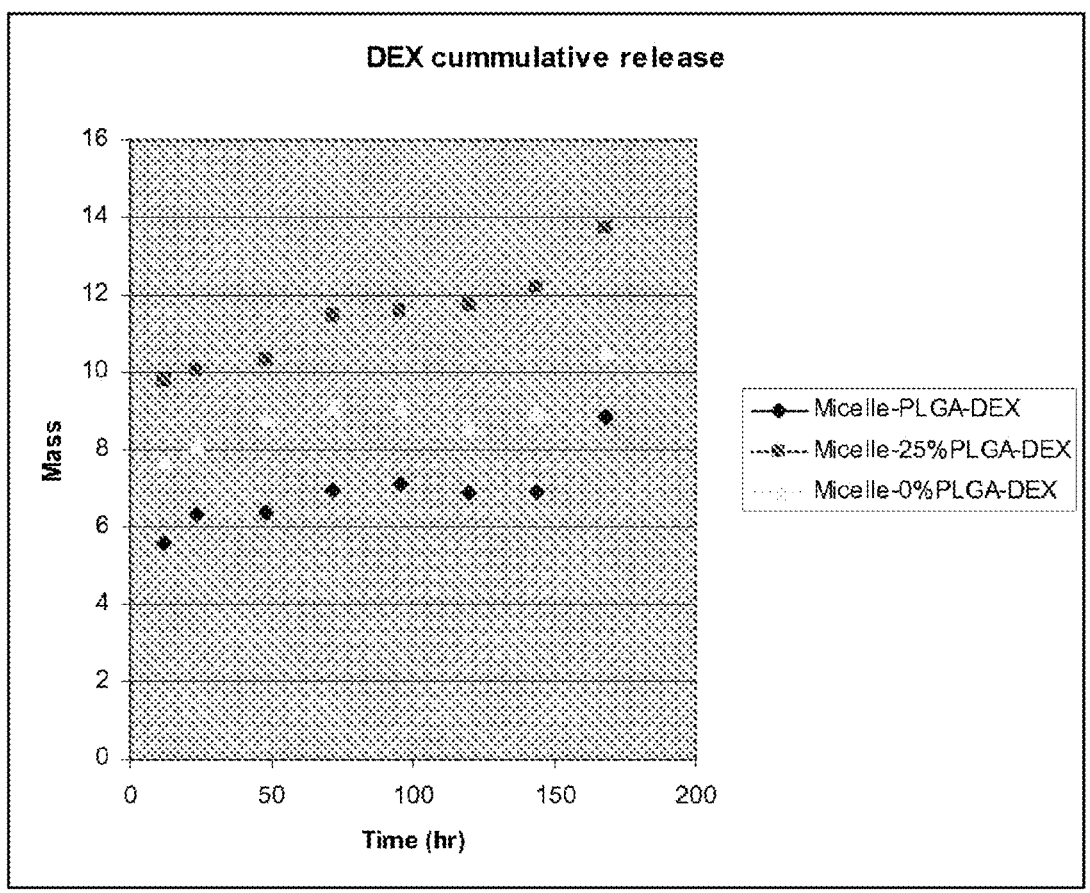
FIG. 14 illustrates the release of an active ingredient (i.e., dexamethasone) from exemplary polymeric nanoparticles formed via self-assembly.

FIG. 14 shows active agent release (i.e., DEX, or dexamethasone, an anti-inflammatory and immunosuppressant drug) from PLGA particles made via self-assembly. The figure illustrates several features of the PLGA particles. First, release is gradual. Second, the release rate can be adjusted by the amount of PLGA in the micelle core without the need to adjust particle size. This is an important advantage compared with conventional PLGA particles or conventional micelles (micelles without PLGA polymers in the central, hydrophobic core), because changing particle size often leads to differential accumulation in the body.

Example 4

Example 4 illustrates one exemplary embodiment of a method of using a nanocomposite particle according to the general inventive concepts described herein.

Bimodal cancer imaging and therapy by a nanocomposite particle. Quantum dots (QDs), superparamagnetic iron oxide nanoparticles (SPIONs), and hyrdophobic anticancer drugs (such as paclitaxel) are co-encapsulated into micelles. The micelles are then conjugated with a ligand recognizing specific receptors on cancer cells. The resulting conjugated micelles are then injected into the bloodstream of a subject. The ligands on the surface of the micelles target the nanocomposite particles to the tumor. Using SPIONs in the nanocomposite particles as contrast agents, a physician can non-invasively image and locate the tumor in deep tissues with MRI. Further, the bright and stable fluorescence generated by the QDs (for example, by a handheld UV lamp) in the nanocomposite particles can guide a surgeon's efforts to remove the tumor during surgery. Although the fluorescence from the QDs does not penetrate to deep tissues as MRI signals do, it offers a convenient way for the surgeon to visualize the tumor during the surgery, as during the surgery the tumor is not in deep tissues anymore and the surgery cannot be performed in an MRI scanner. After the surgery, the anticancer drugs release from the nanocomposite particles to kill possible remaining tumor cells to prevent reemergence of the cancer.

Example 5

Example 5 illustrates one exemplary embodiment of a method of using a nanocomposite particle according to the general inventive concepts described herein.

Multiplexed optical coding of biomolecules by sub-50 nm nanocomposite particles. Quantum dots (QDs) of different emission wavelengths (i.e., different colors) are co-encapsulated into the same micelles. The fluorescent intensity of a particular wavelength of each micelle is proportional to the number of QDs that are encapsulated emitting fluorescence at the particular wavelength. As the ratio of the number of QDs emitting at different wavelengths can be controlled, the ratio can be used as a "coding" mechanism to detect or image multiple types of biomolecules quickly. The size of the nanocomposite particles result in much less steric hindrance in the ligand-target binding.

Example 6

Example 6 illustrates one exemplary embodiment of a method of using a nanocomposite particle according to the general inventive concepts described herein.

Manipulation of single nanocomposite particles for nanofabrication. Nanocomposite particles comprising amphiphilic micelles co-encapsulating quantum dots (QDs) and superparamagnetic iron oxide nanoparticles (SPIONs) are utilized in connection with a nanoconveyor array for manipulation of the nanocomposite particles. The nanoconveyor array may comprise digitized ferromagnetic microdisks or zigzag patterned magnetic nanowire. The very high field gradients at the periphery of each disk or at each zigzag vertex are sufficient to trap the nanocomposite particles. Synchronizing and altering the magnetic fields can control the motion of the nanocomposite particles in the x-y plane, as well as can permit the nanocomposite particles to move from disk to disk, or zigzag vertext to zigzag vertex. While the SPIONs allow for location control by magnetism, the extraordinary brightness and photostability of the QDs allow for the location of the nanocomposite particles to be precisely tracked.

Example 7

Example 7 illustrates one exemplary embodiment of a method of using a nanocomposite particle according to the general inventive concepts described herein.

Nanoscale force sensors for biomechanics studies. As a nanoscale force sensor, nanocomposite particles comprising micelles co-encapsulating quantum dots (QDs) and superparamagnetic iron oxide nanoparticles (SPIONs) are used to identify the biological object to be studied. A well-defined external force is then applied on the biological object by a magnetic micromanipulator, and the change of location of the biological object due to the force is tracked by the fluorescence of the QDs.

What is claimed is:
1. A nanocomposite particle comprising:
   a micelle comprising an amphiphile and a hydrophobic core and a surfactant, where the surfactant is poly(vinyl alcohol);

at least one first hydrophobic quantum dot encapsulated in the hydrophobic core of the micelle, the first quantum dot having a first emission wavelength;

at least one second hydrophobic quantum dot encapsulated in the hydrophobic core of the micelle, the second quantum dot having a second emission wavelength that is different from the first emission wavelength; and the nanocomposite particle having a diameter in a range of about 5 nm to about 1000 nm.

2. The nanocomposite particle according to claim 1 further comprising at least one additional hydrophobic nanoparticle encapsulated in the hydrophobic core of the micelle, the additional nanoparticle selected from the group consisting of metallic nanoparticles, magnetic nanoparticles, carbonaceous nanoparticles, and combinations thereof.

3. The nanocomposite particle according to claim 2, wherein the first emission wavelength is between about 490 nm to about 560 nm and the second emission wavelength is between about 590 nm to about 700 nm.

* * * * *

UNITED STATES PATENT AND TRADEMARK OFFICE
CERTIFICATE OF CORRECTION

PATENT NO. : 9,550,160 B2
APPLICATION NO. : 13/629552
DATED : January 24, 2017
INVENTOR(S) : Jessica O. Winter et al.

Page 1 of 1

It is certified that error appears in the above-identified patent and that said Letters Patent is hereby corrected as shown below:

In the Specification

Column 1, Line 16, delete "This invention is supported, at least in part, by Grant Nos. CBET-0707969, CMMI-090037, and EEC-0914790 awarded by the National Science Foundation. The government has certain rights in the invention." and insert -- This invention was made with government support under grant number CBET0707969 awarded by the National Science Foundation. The government has certain rights in the invention. --

Signed and Sealed this
Eleventh Day of August, 2020

Andrei Iancu
*Director of the United States Patent and Trademark Office*